(12) United States Patent
Saha et al.

(10) Patent No.: US 10,781,315 B2
(45) Date of Patent: Sep. 22, 2020

(54) OPTICALLY CLEAR PHOTO-POLYMERIZATION RESISTS FOR ADDITIVE MANUFACTURING OF RADIOPAQUE PARTS

(71) Applicant: Lawrence Livermore National Security, LLC, Livermore, CA (US)

(72) Inventors: Sourabh Kumar Saha, Livermore, CA (US); James Spencer Oakdale, Castro Valley, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 14 days.

(21) Appl. No.: 15/367,069

(22) Filed: Dec. 1, 2016

(65) Prior Publication Data

US 2018/0155472 A1  Jun. 7, 2018

(51) Int. Cl.
| | |
|---|---|
| C09D 4/00 | (2006.01) |
| C07C 51/60 | (2006.01) |
| B33Y 70/00 | (2020.01) |
| C08F 222/18 | (2006.01) |
| C07C 231/02 | (2006.01) |
| C07C 231/12 | (2006.01) |
| B33Y 10/00 | (2015.01) |
| B33Y 80/00 | (2015.01) |

(52) U.S. Cl.
CPC ............... *C09D 4/00* (2013.01); *B33Y 10/00* (2014.12); *B33Y 70/00* (2014.12); *B33Y 80/00* (2014.12); *C07C 51/60* (2013.01); *C07C 231/02* (2013.01); *C07C 231/12* (2013.01); *C08F 222/18* (2013.01)

(58) Field of Classification Search
CPC ..... C08F 122/105; B33Y 80/00; B33Y 10/00; B33Y 70/00; C07C 231/12; C07C 51/60; C07C 231/02; C09D 4/00
See application file for complete search history.

(56) References Cited

U.S. PATENT DOCUMENTS 5,679,710 A    10/1997 Davy et al.
5,780,668 A *   7/1998 Rheinberger .......... A61K 6/083
                                                     433/215

(Continued)

OTHER PUBLICATIONS

Bückmann et al., "Tailored 3D mechanical metamaterials made by dip-in direct-laser-writing optical lithography," Advanced Materials, vol. 24, No. 20, 2012, pp. 2710-2714.

(Continued)

*Primary Examiner* — Jessica M Roswell
(74) *Attorney, Agent, or Firm* — Zilka-Kotab, P.C.

(57) ABSTRACT

According to one embodiment, a method includes contacting a triiodobenzoic acid with an oxalyl chloride in a solvent whereby triiodobenzoyl chloride is formed, contacting diethanolamine with triiodobenzoyl chloride where triiodobenzoic diol amine is formed, and forming an acrylate of triiodobenzoic diol amine with acryloyl chloride where an organoiodine compound is formed. According to another embodiment, an optically clear photopolymer resist blend for additive manufacturing includes a radiopaque pre-polymer compound where the compound includes at least one of the following: iodine, bromine, tin, lead, or bismuth. The resist blend also includes a photoinitiator, a polymerization inhibitor, and a base pre-polymer.

17 Claims, 16 Drawing Sheets

(56) References Cited

U.S. PATENT DOCUMENTS

| | | | |
|---|---|---|---|
| 6,040,408 A * | 3/2000 | Koole | A61L 31/18 |
| | | | 526/292.1 |
| 7,473,417 B2 | 1/2009 | Zeltinger et al. | |
| 9,062,141 B2 * | 6/2015 | Goodrich | A61K 49/0442 |
| 9,789,231 B2 * | 10/2017 | Goodrich | C08F 220/30 |
| 2010/0041789 A1 * | 2/2010 | Neffgen | A61K 6/0017 |
| | | | 523/117 |
| 2012/0292814 A1 | 11/2012 | Spratt et al. | |
| 2014/0106635 A1 * | 4/2014 | Junior | C08L 7/00 |
| | | | 442/1 |
| 2016/0113846 A1 * | 4/2016 | Willner | A61K 6/0005 |
| | | | 433/217.1 |

OTHER PUBLICATIONS

Lusic et al., "X-ray-Computed Tomography Contrast Agents," Chemical Reviews, vol. 113, No. 3, 2013, pp. 1641-1666.

Shah, T.,"Radiopaque Polymer Formulations for Medical Devices," Medical Plastics, 2000, pp. 1-5.

CreativeMaterials, "Radio-Opaque polymeric inks," Creative Materials Inc., May 12, 2015, as retrieved by the Internet Archive Wayback Machine, https://web.archive.org/web/20150512181504/http://www.creativematerials.com/products/radio-opaque-inks/.

Foster Corporation, "Radiopaque Compounds," Foster Biomedical Polymers and Compounds, Sep. 26, 2015, pp. 1-2, as retrieved by the Internet Archive Wayback Machine, http://www.fostercomp.com/products/radiopaque-additives.

Turner, U.S. Appl. No. 15/037,970, filed May 19, 2016.

Chang et al., "Development and Testing of X-Ray Imaging-Enhanced Poly-L-Lactide Bone Screws," PLoS One, vol. 10, No. 10, 2015, pp. 1-12.

Goodrich, U.S. Appl. No. 14/776,875, filed Sep. 15, 2015.

Hagit et al., "Synthesis and Characterization of Dual Modality (CT/MRI) Core Shell Microparticles for Embolization Purposes," Biomacromolecules, vol. 11, No. 6, 2010, p. 1600-1607.

Zaharia et al., "Chemical structure of methylmethacrylate-2-[2',3',5'-triiodobenzoyl]oxoethylmethacrylate copolymer, radio-opacity, in vitro and in vivo biocompatibility," Acta Biomaterialia, 2008, pp. 1762-1769.

Van Hooy-Corstjens et al., "New intrinsically radiopaque hydrophilic microspheres for embolization: synthesis and characterization," Biomacromolecules, vol. 9, No. 1, 2008, pp. 84-90.

Saralidze et al., "Radio-Opaque and Surface-Functionalized Polymer Microparticles: Potentially Safer Biomaterials for Different Injection Therapies," Biomacromolecules, vol. 7, No. 11, 2006, pp. 2991-2996.

Manero et al., "Wear behavior of the pair Ti—6Al—4V-UHMWPE of acrylic bone cements containing different radiopaque agents," J. Biomater. Appl., vol. 18, No. 4, 2004, pp. 305-319.

Saralidze et al., "Injectable Polymeric Microspheres with X-ray Visibility. Preparation, Properties, and Potential Utility as New Traceable Bulking Agents," Biomacromolecules, vol. 4, No. 3, 2003, pp. 793-798.

Davy et al., "X-Ray Opaque Methacrylate Polymers for Biomedical Applications," Polymer International, vol. 43, No. 2, 1997, pp. 143-154.

Moszner et al., "Synthesis and polymerization of hydrophobic iodine-containing methacrylates," Die Angewandte Makromolekulare Chemie, vol. 224, No. 1, 1995, pp. 115-123.

Cumpston et al., "Two-photon polymerization initiators for threedimensional optical data storage and microfabrication," Nature, vol. 398, Mar. 1999, pp. 51-54.

* cited by examiner

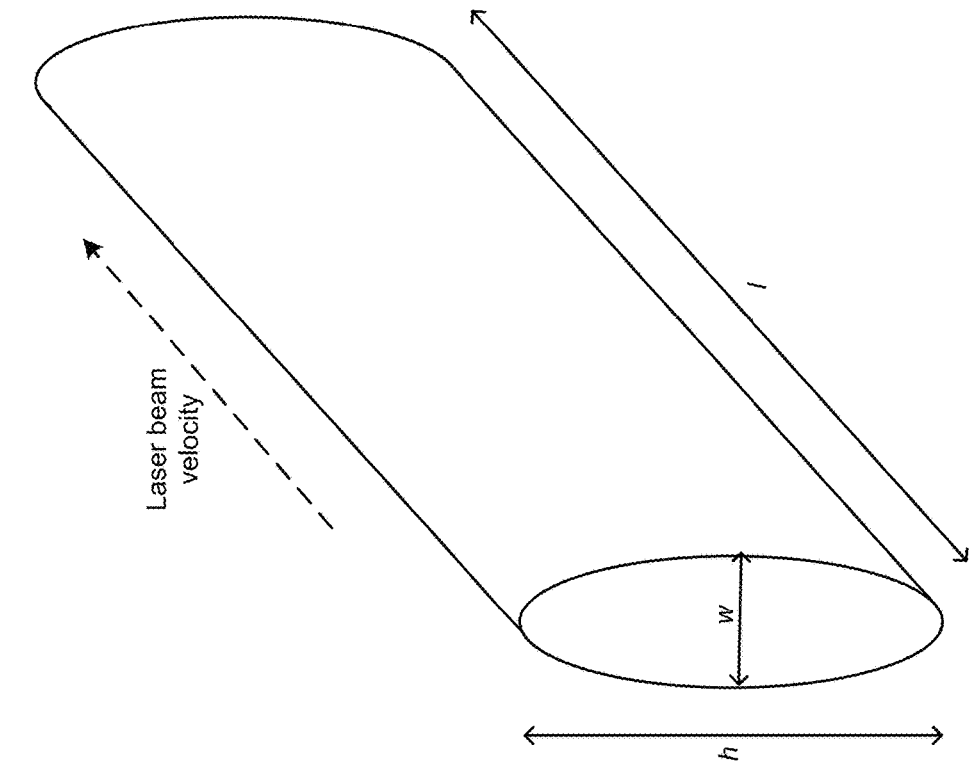
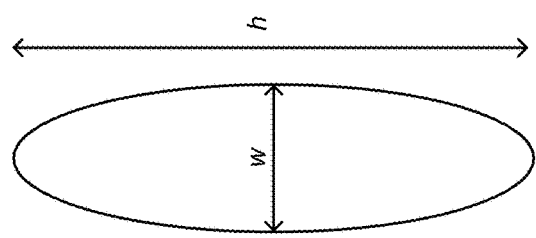
FIG. 2B
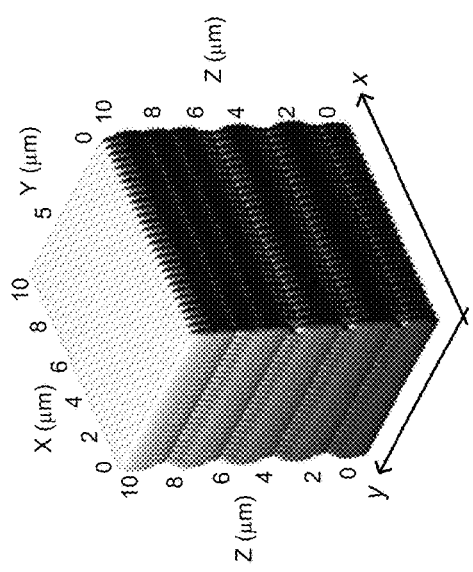
FIG. 2A
FIG. 2C

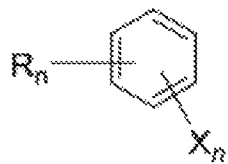

R = defined in FIG. 7B
X = Br, I, Sn, Bi, Pb
n = 1-5

FIG. 7A

R = is defined as follows:

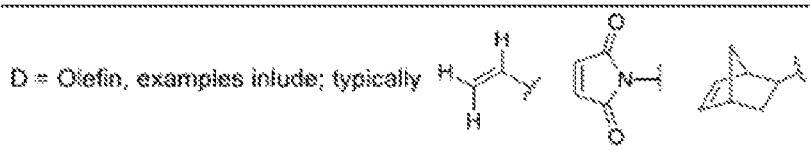

| Acrylic | Epoxy | | Thiol-ene |

X = typically -H or -CH₃, could also include -CₙH₂ₙ₊₁

Y = typically -O- (acrylate) or -NH- (acrylamide), could also include -CH₂-, or -N(CₙH₂ₙ₊₁)-

Z = Aromatic compound containing a covalently bonded high Z element

A = typically -H, could also include -(CₙH₂ₙ₊₁)

D = Olefin, examples include; typically

R' = Linker:   aliphatic: -(CH₂)ₙ-
polyethylene glycol: -(C₂H₄O)ₙ-

Aromatic:   -(CH₂)ₙ—⌬—(CH₂)ₙ-

Phenyl (n = 0), Benzyl (n = 1)     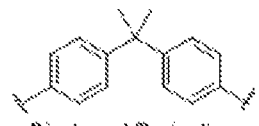 Bisphenol Derivatives

Dimethylsiloxane:   -(SiMe₂O)ₙ-

*Linker may also contain any of the following function groups*
Ester; -RC(O)OR-
Amide; -RC(O)NRₙ- where n = 1 or 2 and R = H or as defined above
Amine; -RNRₙ- where n = 1 or 2 and R = H or as defined above
Ether; -ROR-
Urea; -RₙNC(O)NRₙ- where n = 1 or 2 and R = H or as defined above
Carbamate; -ROC(O)NRₙ- where n = 1 or 2 and R = H or as defined above
Carbonate; -ROC(O)OR-
Sulfone; -RSO₂R-

FIG. 7B

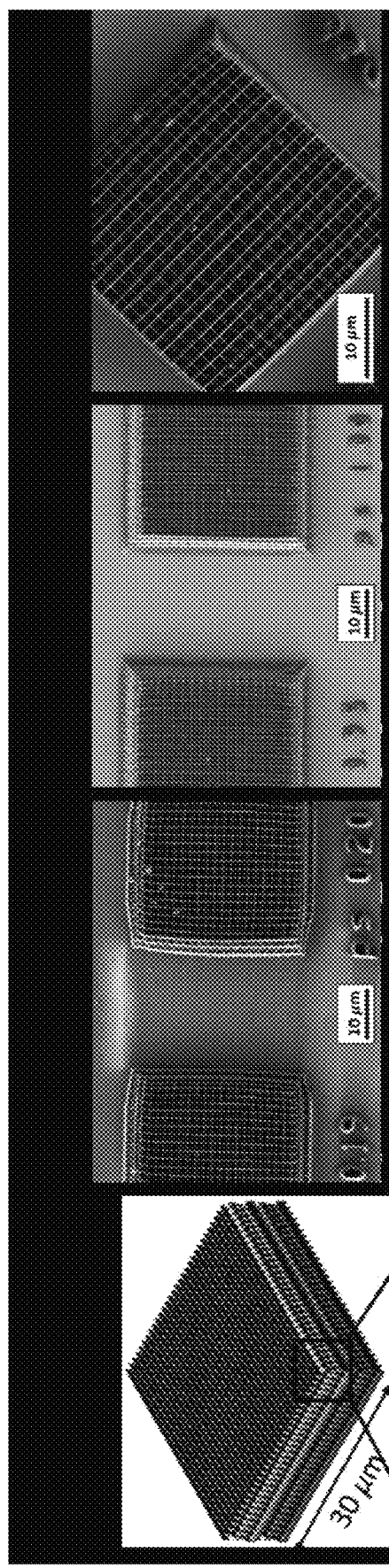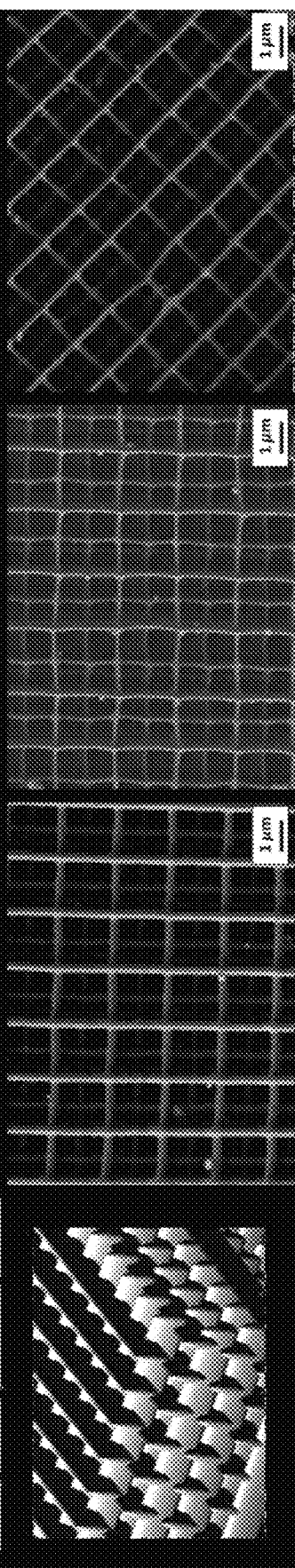

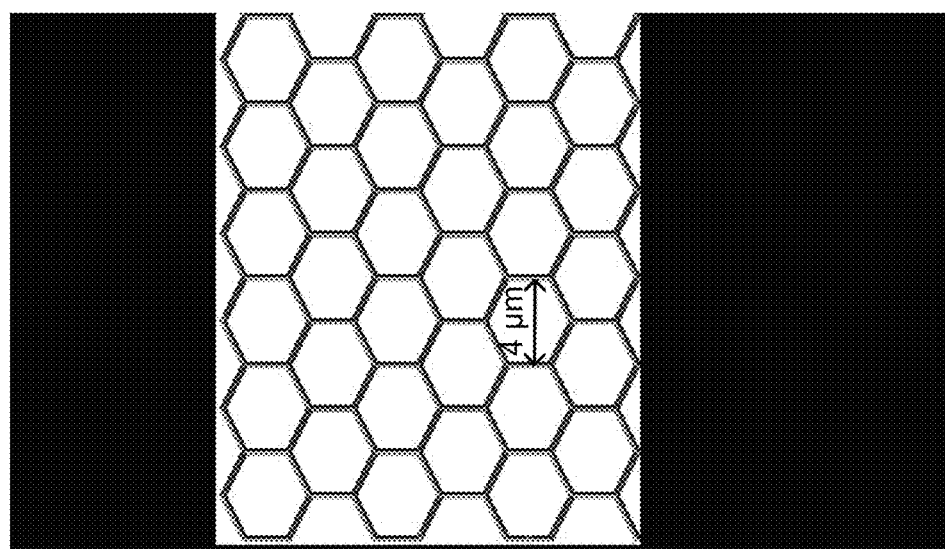
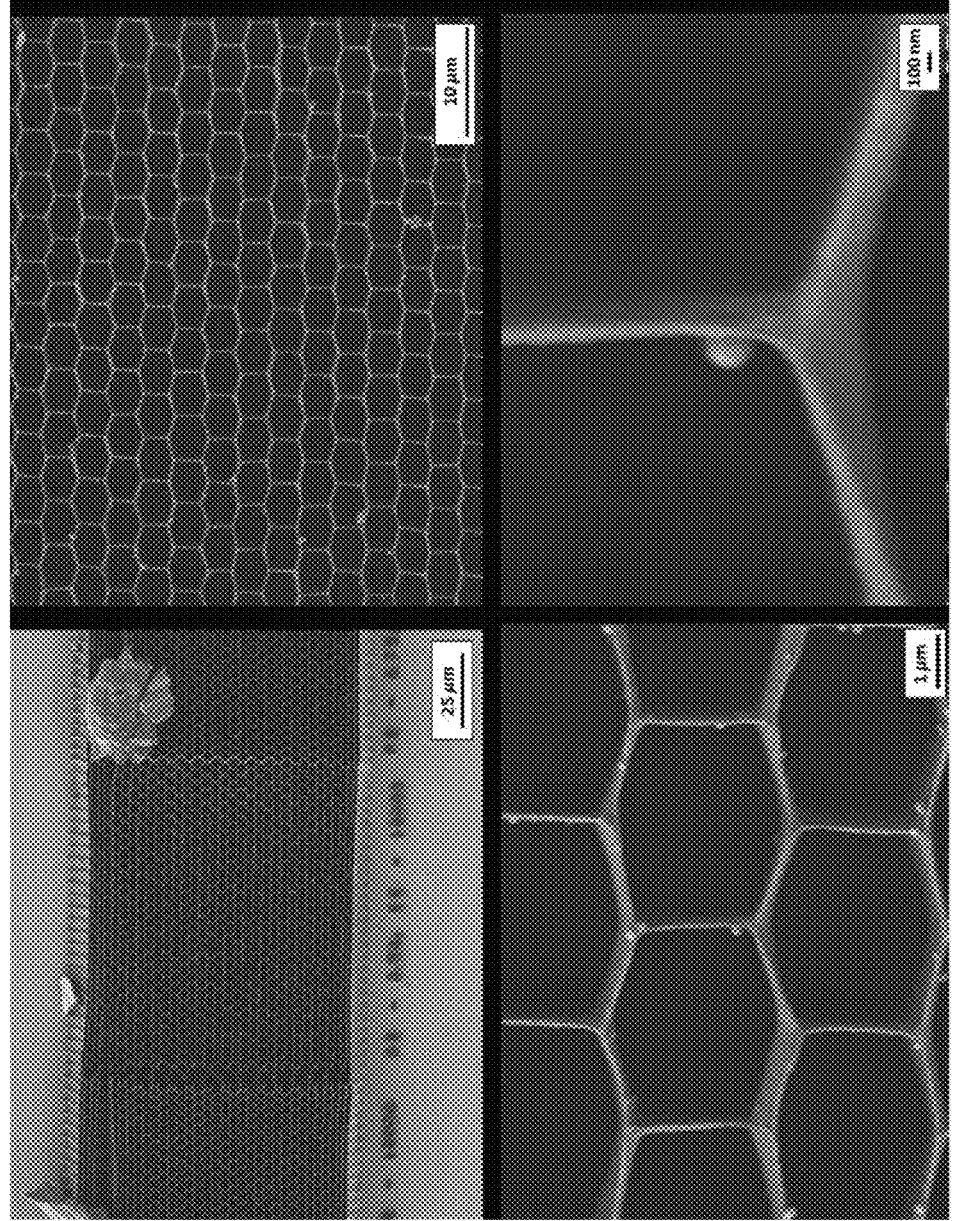
FIG. 14E
FIG. 14B
FIG. 14D
FIG. 14A
FIG. 14C

OPTICALLY CLEAR PHOTO-POLYMERIZATION RESISTS FOR ADDITIVE MANUFACTURING OF RADIOPAQUE PARTS

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to photo-polymerization based additive manufacturing techniques, and more particularly, this invention relates to optically clear photo-polymerization resists for additive manufacturing of radiopaque parts.

BACKGROUND

X-ray computed tomography (CT) is an established 3D imaging technique for evaluating the interior of an object in a nondestructive manner. X-ray images are obtained from several different angles to produce cross-sectional images, referred to as tomographic slices. In clinical settings, CT is often the first choice as rapid-feedback, noninvasive diagnostic of interior tissues/organ systems, such as the gastrointestinal tract, lungs, liver, and bone. Likewise, material science relies on the imaging capacity of CT for accessing material properties such as homogeneity, density, and composition. In addition, CT may reveal the presence of potential hidden defects beneath the surface of materials.

The extent to which a material absorbs X-rays is expressed by the X-ray absorption coefficient ($\mu$) and is directly related to the atomic number (Z) and density ($\rho$) of the material as shown in Equation 1 below:

$$\mu = \frac{\rho Z^4}{AE^3} \qquad \text{Equation 1}$$

Here, A is the atomic mass and E is the X-ray energy; thus, Equation 1 shows that X-ray absorption ($\mu$) is influenced significantly by the atomic number (Z).

Biological tissue and most polymeric materials are comprised primarily of elements with a low Z value: hydrogen, carbon, nitrogen, and oxygen. As a result, these materials are generally radiolucent and appear relatively transparent in reconstructed CT images. In a clinical setting, in order to improve contrast between various tissues, radiopaque imaging agents, most commonly iodine and barium, are used. In addition to iodine and barium, lanthanide-based complexes, gold nanoparticles, and xenon gas have been used for contrast enhancement in CT imaging.

In material science, phase contrast enhancers are less constrained by biocompatibility issues and may be determined by specific applications. However, methods to add high-Z containing salts to materials may not guarantee the product remains optically clear or that the iodine/barium atoms are homogenously and chemically bonded during photo curing.

Radiopacity of polymer parts fabricated by additive manufacturing (AM) techniques enables non-destructive imaging of internal features of AM parts by X-ray CT imaging. Conventional resists are unsuitable for CT imaging because the low atomic number of the constituents of a typical organic compound includes carbon, hydrogen, nitrogen, and oxygen atoms. Due to the low atomic number (Z number), these polymer materials absorb X-rays poorly and appear relatively transparent in the CT images. Thus, it is not possible to verify whether a fabricated AM part meets the design tolerances, thereby severely limiting the adoption of AM fabrication of functional parts.

One technique to increase the average atomic number of the constituents is to add components (i.e. contrast agents) containing iodine or barium that have high-atomic numbers. Although this approach of physically mixing in high-Z material works for medical CT imaging, it is ineffective in creating radiopaque raw materials for additive manufacturing.

Challenges in creating radiopaque AM resists arise from these parameters: a) one should be able to locally polymerize the resist via light (instead of bulk polymerization) so that polymer parts can be additively manufactured by joining the distinct building blocks, b) the high-Z contrast agent should be homogenously mixed throughout the final AM part, and c) the concentration of the contrast agent should be insensitive to polymerization and post-processing steps, i.e., the contrast agent should not be "washed out" during development. In addition, the resists that are used for two-photon polymerization based submicron AM must be optically clear. Thus, the techniques and formulations used as contrast enhancement agents in the X-ray CT medical imaging field are not appropriate for additive manufacturing.

SUMMARY

According to one embodiment, a method includes contacting a triiodobenzoic acid with an oxalyl chloride in a solvent whereby triiodobenzoyl chloride is formed, contacting diethanolamine with triiodobenzoyl chloride where triiodobenzoic diol amine is formed, and forming an acrylate of triiodobenzoic diol amine with acryloyl chloride where an organoiodine compound is formed.

According to another embodiment, an optically clear photopolymer resist blend for additive manufacturing includes a radiopaque pre-polymer compound where the compound includes at least one of the following: iodine, bromine, tin, lead, or bismuth. The resist blend also includes a photoinitiator, a polymerization inhibitor, and a base pre-polymer.

According to yet another embodiment, a method of forming an optically clear resist blend for a lithography process involves diluting an iodinated pre-polymer compound in a first solvent, adding a base pre-polymer to the diluted iodinated pre-polymer compound in first solvent, and removing the first solvent from a mixture of the base pre-polymer and the iodinated pre-polymer compound. Furthermore, the method includes dissolving a photoinitiator in a second solvent and then adding the photoinitiator in a second solvent to the mixture of base pre-polymer and iodinated pre-polymer. The insoluble particulate matter from the mixture of base pre-polymer, iodinated pre-polymer, and photoinitiator in the second solvent is removed by centrifugation. An additive pre-polymer is added to tune a refractive index of the resist blend to be about equal to a refractive index of an objective lens of the lithography process.

Other aspects and advantages of the present invention will become apparent from the following detailed description, which, when taken in conjunction with the drawings, illustrate by way of example the principles of the invention.

BRIEF DESCRIPTION OF THE DRAWINGS

FIG. 2A-2B are schematic drawings of building blocks printed during two photon polymerization lithography.

FIG. 2C is a schematic drawings of log-pile structure printed during two photon polymerization lithography

FIG. 7A is a schematic drawing of aromatics with covalently bonded high-Z elements according to various embodiments.

FIG. 7B is a schematic drawing of chemical components of the high-Z-element pre-polymer compound according to various embodiments.

FIGS. 13A-13B are CAD drawing of 3D printed parts according to one embodiment.

FIGS. 13C-13D are scanning electron microscope images of 3D parts printed by conventional mode of TPP lithography according to one embodiment.

FIGS. 13E-13F are scanning electron microscope images of 3D parts printed by dip-in of TPP lithography according to one embodiment.

FIGS. 13G-13H are scanning electron microscope images of 3D parts printed by dip-in of TPP lithography according to one embodiment.

FIGS. 14A-14D are scanning electron microscope images of 3D parts printed by dip-in of TPP lithography according to one embodiment.

FIG. 14E is a CAD drawing of 3D printed part according to one embodiment.

DETAILED DESCRIPTION

Figure 1:
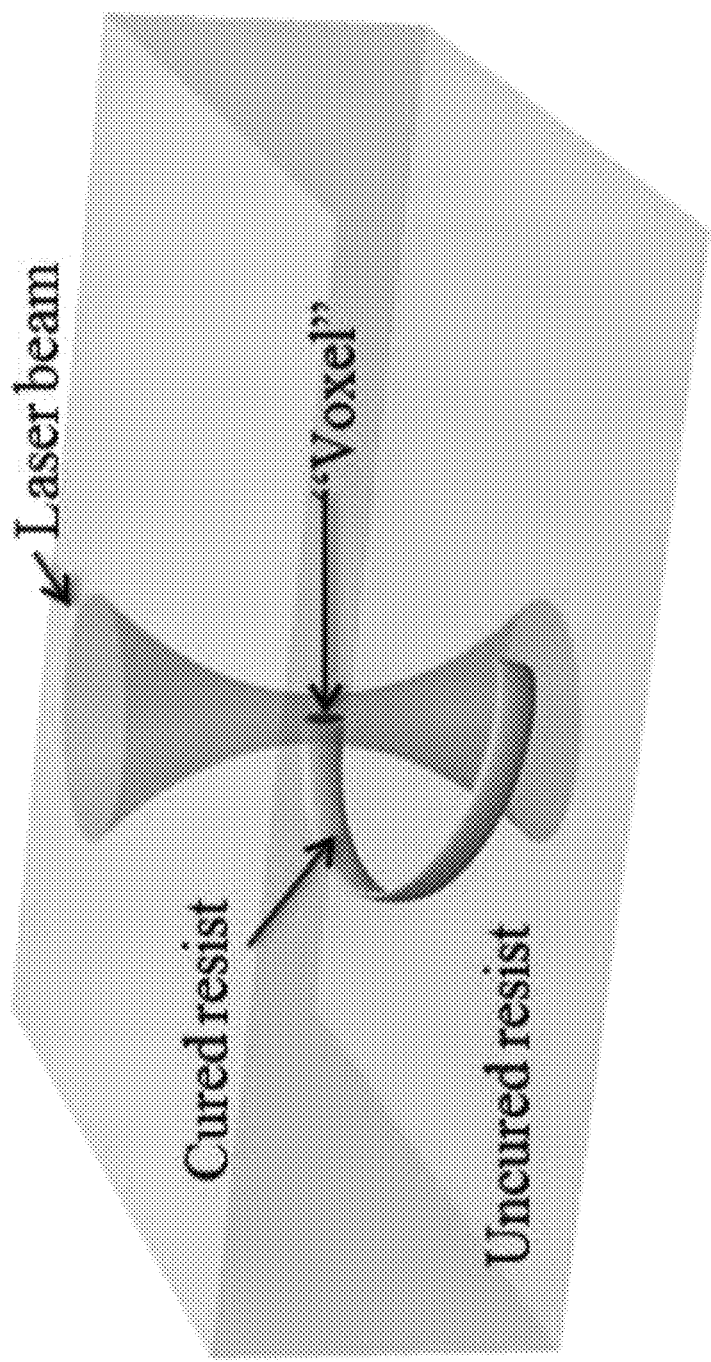
FIG. 1 is a schematic drawing of two photon polymerization lithography.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description discloses several preferred embodiments of an optically clear, radiopaque resist blend and/or related systems and methods.

In one general embodiment, a method includes contacting a triiodobenzoic acid with an oxalyl chloride in a solvent whereby triiodobenzoyl chloride is formed, contacting diethanolamine with triiodobenzoyl chloride where triiodobenzoic diol amine is formed, and forming an acrylate of triiodobenzoic diol amine with acryloyl chloride where an organoiodine compound is formed.

In another general embodiment, an optically clear photopolymer resist blend for additive manufacturing includes a radiopaque pre-polymer compound where the compound includes at least one of the following: iodine, bromine, tin, lead, or bismuth. The resist blend also includes a photoinitiator, a polymerization inhibitor, and a base pre-polymer.

In yet another general embodiment, a method of forming an optically clear resist blend for a lithography process involves diluting an iodinated pre-polymer compound in a first solvent, adding a base pre-polymer to the diluted iodinated pre-polymer compound in first solvent, and removing the first solvent from a mixture of the base pre-polymer and the iodinated pre-polymer compound. Furthermore, the method includes dissolving a photoinitiator in a second solvent and then adding the photoinitiator in a second solvent to the mixture of base pre-polymer and iodinated pre-polymer. The insoluble particulate matter from the mixture of base pre-polymer, iodinated pre-polymer, and photoinitiator in the second solvent is removed by centrifugation. An additive pre-polymer is added to tune a refractive index of the resist blend to be about equal to a refractive index of an objective lens of the lithography process.

A list of acronyms used in the description is provided below.

3D Three dimensional
AM Additive Manufacturing
BPA Bisphenol A ethoxylate diacrylate
CAD Computer-aided Design
CT Computed Tomography
DEA Diethanolamine
DiLL Dip in Laser Lithography
DMF Dimethylformamide
DPEP/HA Dipentaerythritol penta/hexa-acrylate
LAC Linear attenuation coefficient
MAC Mass attenuation coefficient
MEHQ 4-methoxyphenol
μm micron nm nanometer
NA Numerical Aperture
PETA Pentaerythritol triacrylate
SEM Scanning Electron Micrograph
THF Tetrahydrofuran
TMPTA Trimethylpropane triacrylate
TPP Two photon polymerization
UV Ultraviolet Two photon polymerization (TPP) lithography is a direct laser write process that enables fabrication of millimeter scale three dimensional (3D) structures with submicron building blocks. In this technique, writing is achieved via a nonlinear two photon absorption process in which two photons are near-simultaneously absorbed at high laser intensities.

FIG. 1 shows a schematic drawing of additive manufacturing (AM) via TPP lithography that occurs in the interior of the resist. During direct laser writing, submicron volume pixel ("voxel") features are printed in the interior of the photopolymer resist material via localized polymerization reactions that are initiated by two-photon absorption of the incident light. Due to localized polymerization, the solubility of the resist material in a solvent changes to such an extent that this localized region withstands the development process. During the development process, the unexposed regions of the photopolymer material are either selectively "washed away" by dissolving in an appropriate solvent (negative resist) or remain undissolved (positive resist). The development process leaves behind individual exposed voxels that may be resistant to dissolution in solvent (negative resist) or may be formed from dissolution of exposed regions thereby leaving vacant exposed regions (positive resist). The exposed voxel features have an oval cross-section that is determined by the light intensity profile in the resist when the laser beam is focused on a spot using an objective lens.

A schematic of the two types of building blocks generated during TPP are shown in FIGS. 2A and 2B. A stationary laser beam generates an ellipsoidal voxel feature (FIG. 2A). A moving laser beam generates a line features with an ellipse cross-section (FIG. 2B). The width (w) of the features may vary from about 100 nm to 2 μm and the height (h) of the features may vary from 2 to 6 times the width. FIG. 2C is an example of an additive manufactured part shown as a log-pile structure generated by overlapping multiple ellipsoidal lines (FIG. 2B). The aspect ratio (h/w) reduces with an increase in numerical aperture (NA) of the objective lens.

Figure 3B:
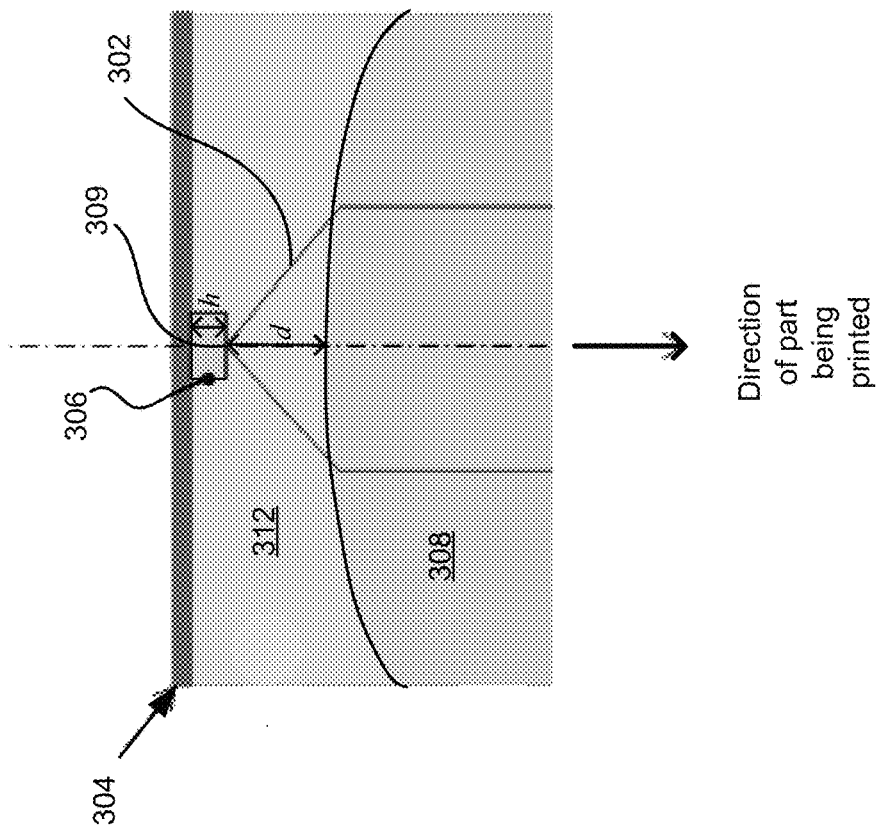
FIG. 3B is a schematic drawing of the dip-in mode of two photon polymerization lithography.
Figure 3A:
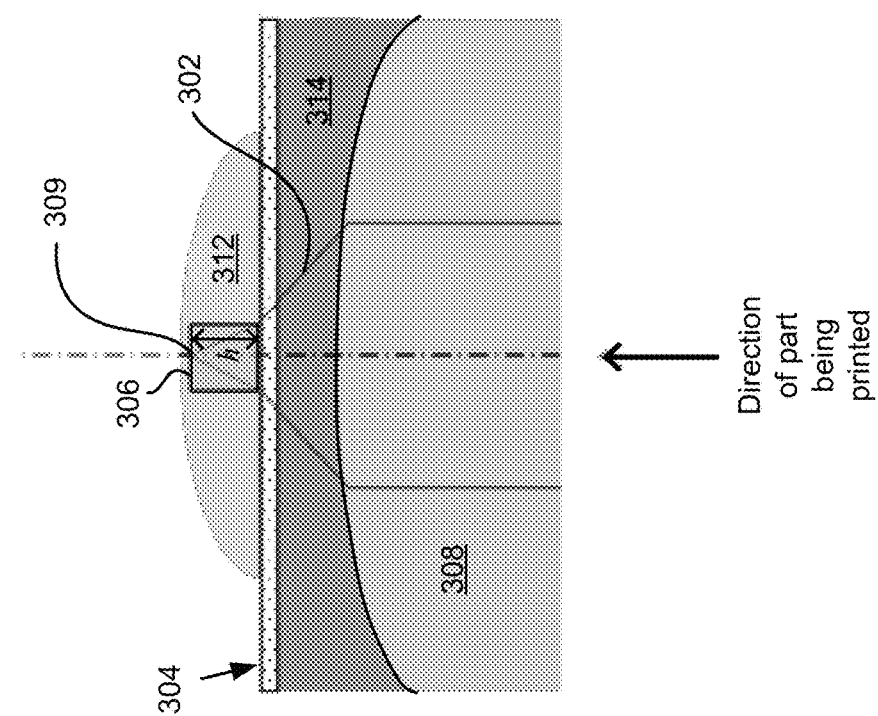
FIG. 3A is a schematic drawing of the conventional mode of two photon polymerization lithography.

There are two different writing modes that may be used for TPP lithography: conventional mode and dip-in mode. Schematic representations of each of these modes are shown in FIGS. 3A and 3B. In the conventional mode (FIG. 3A) the laser beam 302 travels through immersion oil 314 and an optically transparent substrate 304 layer, for example, a glass slide, before initiating local polymerization. The part 306 is built in a layer-by-layer fashion within the resist 312 by progressively moving the objective lens 308 closer to the substrate 304 layer through the immersion oil 314. Thus, in this mode, the height h of the printed part 306 is limited by the working distance of the objective lens 308 (typically a few hundred microns). Eventually during printing, the objective lens 308 may physically stop at the substrate 304 layer thereby preventing any further printing.

In addition, during printing the height h of the part 306 may be substantially lower than the limit determined by the physical stop of the objective lens at the substrate 304 layer. The light intensity from the laser beam 302 shining up through the part 306 is increasingly diminished by the increasing height h of the part 306 during printing thereby causing the subsequent printing to become non-uniform. As the laser beam 302 passes through the polymerized material of the printed part 306, the intensity of the focal spot 309 decreases with an increase in height h of the printed part 306. Thus, the conventional mode of TPP is limited to generating parts with a height of about tens of microns.

Moreover, the conventional mode of TPP depends on a clear substrate, for example glass, so the laser beam may pass through. Thus, writing on opaque substrates such as opaque silicon or metal is not possible.

The conventional mode of TPP is useful for testing the feasibility of printing with a new resist that does not have the same refractive index as the objective lens. Printing in the conventional mode which produces parts with a limited height may not be adversely affected by mismatch between the refractive index of the resist and the objective lens. For printing taller parts in the dip-in mode, however, a mismatch in the refractive index may lead to spherical aberrations that degrade the printing performance of the taller printed parts.

A schematic representation of the dip-in mode (for example, DiLL, Dip-in Laser Lithography) of TPP lithography is shown in FIG. 3B. The resist 312 may sit directly on the objective lens 308 and the focal spot 309 of the beam 302 is located at a working distance d away from the objective 308 exterior surface. The part 306 is built in a layer-by-layer fashion by progressively driving the objective lens 308 away from the substrate 304 layer. The height h of the printed part 306 is not limited by the working distance of the objective lens 308 since the objective lens 308 moves away from the substrate 304 with the increasing height h of the printed part 306. Thus millimeter tall structures can be printed in the dip-in mode. Moreover, parts 306 may be printed on top of a substrate 304 composed of opaque materials such as silicon, metals, etc.

Since the objective lens contacts the resist during printing in the dip in mode, optimal printing may occur when the refractive indices of the resist and the objective lens are the same, and ideally, the resist is optically transparent. If the refractive index of the resist 312 and objective lens 308 do not match, spherical aberrations may occur and may cause large distortions in the printed part 306.

Furthermore, parts generated with conventional resists, such as the Nanoscribe photoresist IP-DIP, using the dip-in mode have features composed primarily of hydrogen, carbon, nitrogen, and oxygen-atoms with low Z values and thus low X-ray attenuation values. Therefore, these 3D structures, including the voxel features, are virtually transparent to X-ray CT imaging.

Thus, it would be desirable to provide a photoresist that generates not only tall parts with submicron features using the dip-in mode of TPP lithography but also radiopaque 3D parts that may be visualized by CT imaging. Various embodiments described herein provide an optically clear radiopaque photopolymer resist for AM by mixing in an optically clear organoiodine compound to a resist blend optimized for localized curing. The optically clear iodine-doped resist blend described herein increases the mean atomic number of the part fabricated by AM. In addition, the resist may act as both a pre-polymer and a contrast agent. Moreover, during AM the organoiodine compound may be chemically bonded with the other pre-polymer/monomer components of the resist blend to form cross-linked polymer chains at the scale of the submicron and micron building blocks of the final polymerized part. Thus, the iodine atoms may be homogenously distributed throughout the part and may not be physically "washed out" during post-processing development. The radiopaque part may be imaged by X-ray CT to inspect the internal features of the additive manufactured part.

Figure 4:
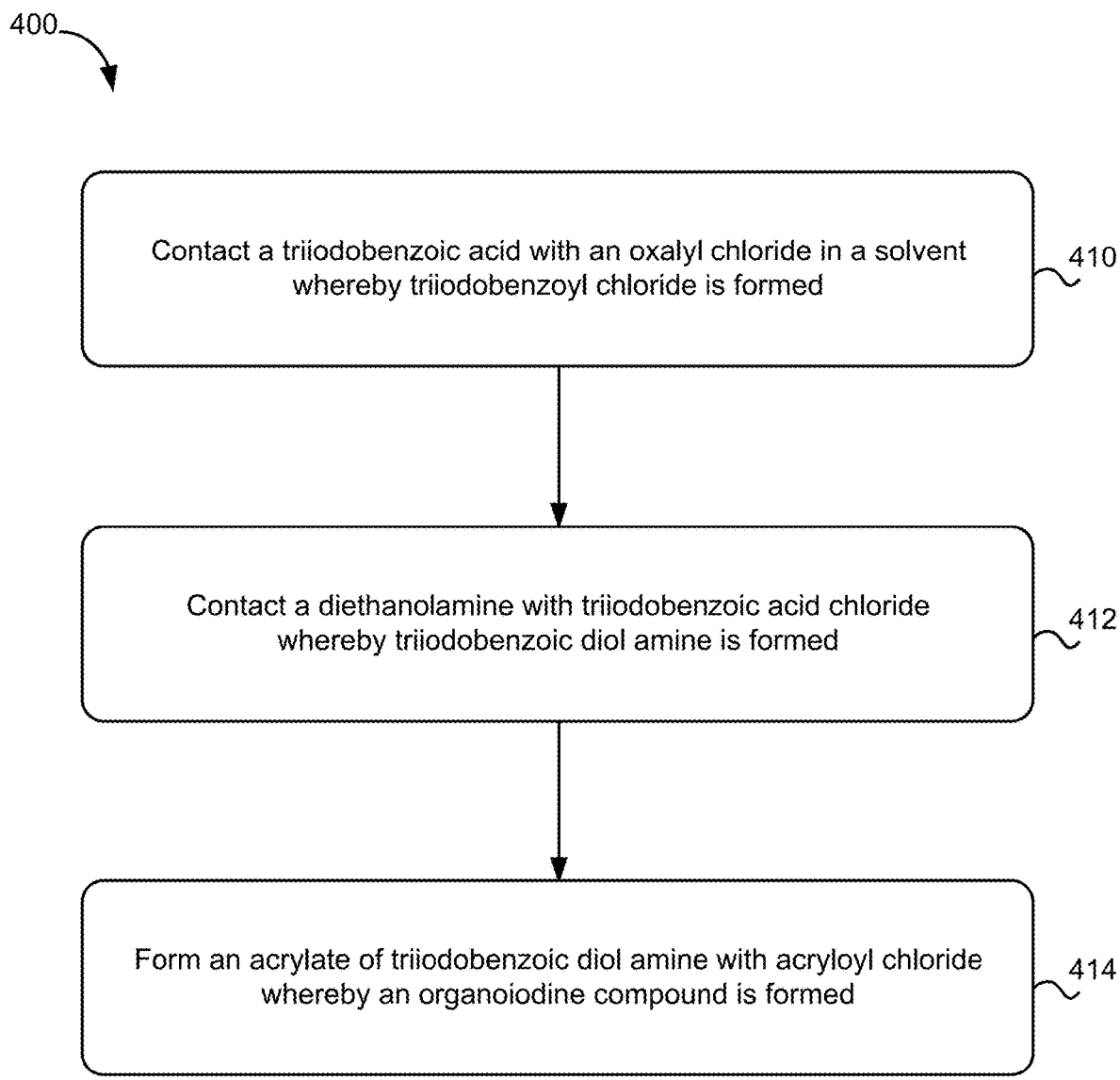
FIG. 4 is a flow diagram of the formation of an organoiodine compound according to one embodiment.

FIG. 4 shows a flowchart for the method 400 for forming an organoiodine compound, in accordance with one embodiment. As an option, the present method 400 may be implemented to form organoiodine compound such as those shown in the other FIGS. described herein. Of course, however, this method 400 and others presented herein may be used to form compounds which may or may not be related to the illustrative embodiments listed herein. Further, the methods presented herein may be carried out in any desired environment. Moreover, more or less operations than those shown in FIG. 4 may be included in method 400, according to various embodiments. It should also be noted that any of the aforementioned features may be used in any of the embodiments described in accordance with the various methods.

As shown in FIG. 4, one embodiment of method 400 begins with step 410 in which contacting a triiodobenzoic acid with an oxalyl chloride in a solvent may form triiodobenzoyl chloride. Looking to FIG. 5, and exemplary example 500 of method 400 shows 2,3,5-triiodobenzoic acid 502 contacting with an oxalyl chloride, (COCl)$_2$, in a solvent where triiodobenzoyl chloride 504 is formed. In some approaches, the solvent used in step 410 may be dimethylformamide (DMF). In other approaches, the solvent used in step 410 may be tetrahydrofuran (THF).

In one embodiment of method 400 shown in FIG. 4, step 412 involves contacting diethanolamine with triiodobenzoyl chloride where triiodobenzoic diol amine may be formed. In some approaches, the contacting in step 412 may occur in the presence of a solvent, for example THF. In other approaches, the contacting in step 412 may occur in the presence of triethylamine (Et$_3$N). As illustrated in example 500 in FIG. 5, step 412 may form triiodobenzoic diol amine 506.

In one embodiment of method 400 in FIG. 4, step 414 involves forming a diacrylate of triiodobenzoic diol amine with acryloyl chloride where an organoiodine compound may be formed. In some approaches, the acrylation of triiodobenzoic diol amine in step 414 may occur in the presence of a solvent, for example THF. In other approaches, acrylation of triiodobenzoic diol amine in step 414 may occur in the presence of a N,N-diisopropylethylamine (DIPEA). As shown in example 500 in FIG. 5, forming an acrylate of triiodobenzoic diol amine 506 following step 414 of method 400 in FIG. 4, may form an organoiodine compound 508. The organoiodine compound 508, an I$_3$-oligomer, may contain 54.78% iodine by mass and may be extremely viscous or a solid and slightly yellow in color.

In some embodiments, the organoiodine compound 508 may be an iodine pre-polymer. In other embodiments, the organoiodine compound 508 may be a contrast agent.

Figure 5:
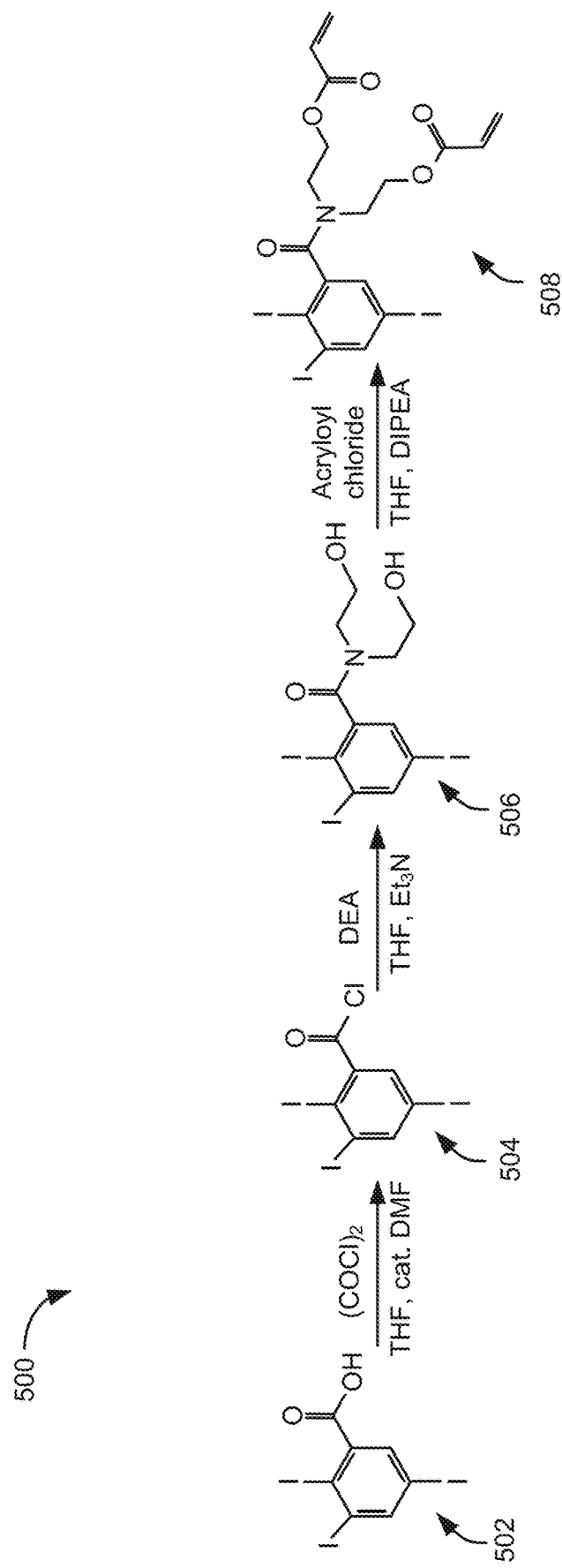
FIG. 5 is a schematic drawing of the formation of an organoiodine compound according to one embodiment.

One exemplary embodiment of method 400 as illustrated in example 500 in FIG. 5 includes an iodinated pre-polymer compound 508 having the following structural formula:

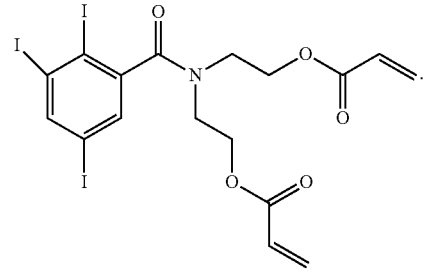 [SMILES: C=CC(=O)OCCN(CCOC(=O)C=C)C(=O)c1cc(I)cc(I)c1I]

Moreover, the organoiodine compound 508 may be further characterized as a covalently-bonded, iodinated-aromatic acrylate oligomer. In some embodiments, the iodinated pre-polymer compound 508 may contain iodine in a range of about 53 wt % to about 56 wt % based on a total weight of the compound. In another embodiment, the iodinated pre-polymer compound 508 may be in liquid form. In yet another embodiment, the iodinated pre-polymer compound 508 may be soluble in a base pre-polymer.

A resist blend for TPP lithography preferably includes the following three components: photoinitiator, inhibitors, and radiopaque pre-polymer. The photoinitiator absorbs incident radiation and generates a reactive species that in turn initiates the polymerization reaction in the pre-polymer. Polymerization of the pre-polymer leads to an increase in the molecular weight as the cross linking of the material causes the change in physical phase from liquid to solid state. The pre-polymer may include two components: a reactive species for initiating polymerization upon application of energy and an inhibitor in a low concentration for terminating polymerization. The concentration of inhibitor determines the amount of energy required to initiate polymerization of the pre-polymer. In addition, the resist blend may also include an additional inhibitor. The total concentration of inhibitor controls the extent of the polymerization of the resist and thus the size of the voxel. Moreover, the inhibitors extend the pot life of the resist by preventing premature curing.

The radiopaque pre-polymer, according to a preferred embodiment, is an iodinated pre-polymer, and therefore many of the embodiments described herein refer to iodine and an iodinated pre-polymer. This is done by way of example only and should not be deemed limiting. Rather, as described herein, the radiopaque pre-polymer may include elements other than iodine to provide the radiopacity. Accordingly, the described instances of iodinated pre-polymer may be substituted in various embodiments with other types of radiopaque pre-polymers as described herein.

TABLE 1

Figure 12:
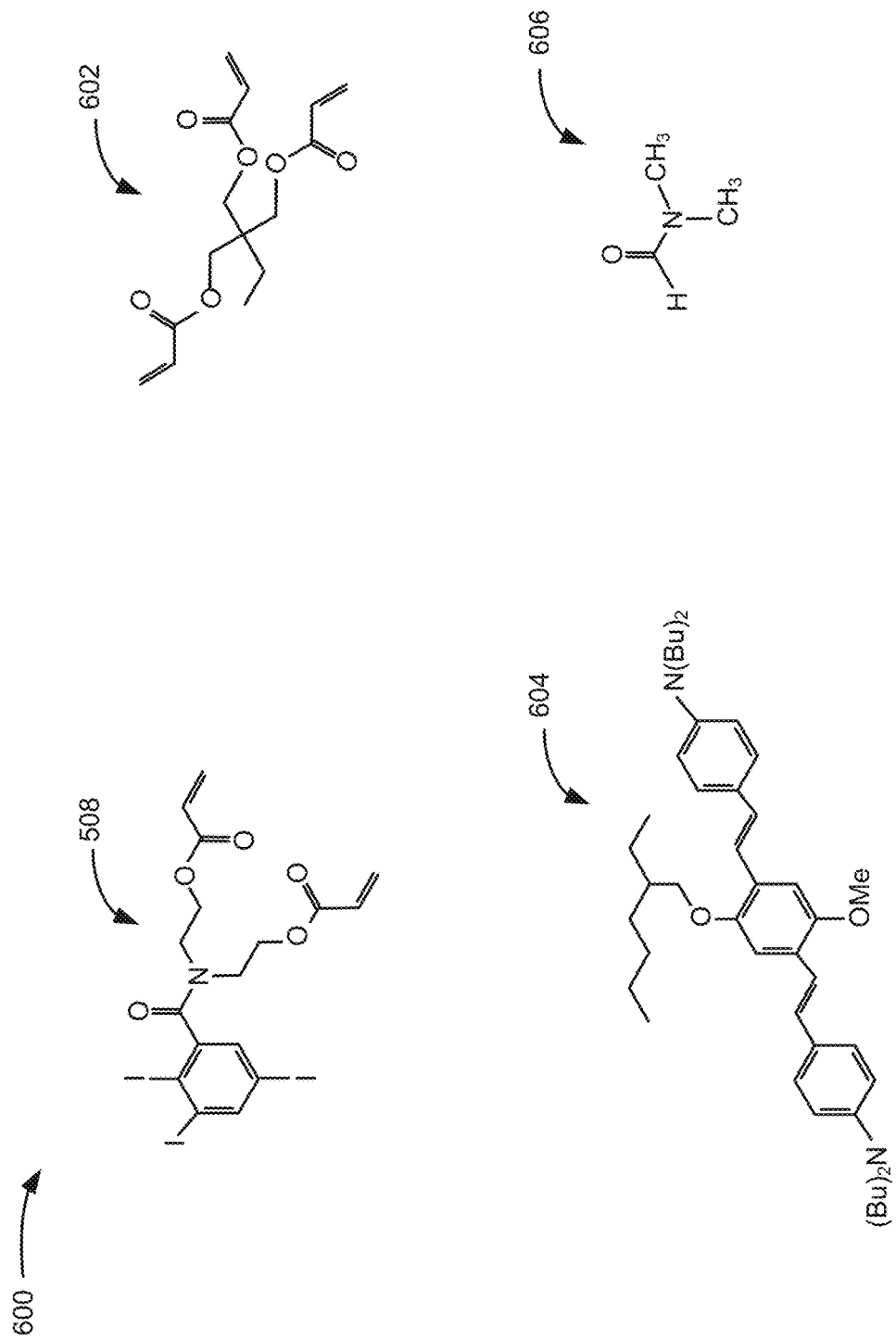
FIG. 12 is a schematic drawing of the components of an optically clear, radiopaque resist blend according to one embodiment.

| Functional Components of Resist Blend | | | | |
|---|---|---|---|---|
| # | Type | Function | Examples | Synthesis |
| 1 | Photoinitiator | To absorb light and generate reactive species | 604, FIG. 12 | Based on published literature |
| 2 | Base Pre-polymer | To form the backbone of the cured material | TMPTA, 602, FIG.2 PETA, DPEP/HA | Commercially available |
| 3 | Iodinated Pre-polymer | To make the polymerized material radiopaque | 508, FIGS. 5 and 12 | Newly synthesized |

TABLE 1-continued

Functional Components of Resist Blend

| # | Type | Function | Examples | Synthesis |
|---|------|----------|----------|-----------|
| 4 | Additive Pre-polymer | To tune the refractive index of the resist blend | BPA | Commercially available |
| 5 | Inhibitor | To control the extent of polymerization, extend pot-life | MEHQ | Commercially available |
| 6 | Solvent | To increase solubility of iodinated pre-polymer in the resist blend | DMF | Commercially available |

TABLE 2

Design Rules for Components of Resist Blend

| # | Component | Desired Property | Tuned by: | Selection guideline |
|---|-----------|------------------|-----------|---------------------|
| 1 | Photoinitiator | High 2-photon cross section & preferentially generates radicals instead of fluorescence | Molecular structure of photoinitiator | Efficiency is high enough to cause polymerization with femtosecond oscillator laser sources. |
| 2 | Base Pre-polymer | High strength | Strength: number of functional groups | Higher number of acrylate groups preferable |
|   |                  | High viscosity | Viscosity: hydrogen bonding and size of pre-polymer | Hydrogen bonding for higher viscosity |
| 3 | Iodinated Pre-polymer | Low iodine reactivity | Iodine bonding to aromatic group | Select a densely substituted aromatic iodine. Alkyl iodines are too reactive. |
|   |                       | High solubility in base pre-polymer | Matching Hildebrand solubility parameter | Specific compound selected based on inexpensive and commercially available precursor |
| 4 | Additive Pre-polymer | To obtain refractive index (RI) = 1.52 | Alkyl pre-polymers have low RI, Aromatic pre-polymers have high RI | To reduce RI: add alkyl pre-polymers  To increase RI: add aromatic pre-polymers |
| 5 | Inhibitor | Effective stabilizer | Already present in commercial pre-polymers | |
| 6 | Solvent | To increase solubility | | The boiling point/vapor pressure of the solvent additive is high. Low boiling point solvents tend to evaporate during the printing process leading to precipitation of resin components. |

The resist blend may be tuned by adding components, for example, other pre-polymers, inhibitor, solvent, and/or dispersed solid additives. The functional components of the radiopaque resist blend according to various embodiments described herein are summarized in Table 1. The design rules for selection of the six functional components of the radiopaque resist blend are summarized in Table 2. According to various embodiments, components of the resist blend may be tuned for optimal printing of radiopaque parts by two photon polymerization.

The sections that follow describe ratio and design rules for components of resist blend according to various embodiments.

Design Rules for the Base Pre-Polymer

Referring to Table 1 and Table 2, the base pre-polymer of the resist blend forms the backbone of the cured material. Thus, the viscosity of the uncured resist and the strength of the cured resist may be tuned by selecting the appropriate base pre-polymer for the resist blend.

Tuning the Strength of the Cured Resist

The extent of resolution of the printed part using a radiopaque resist blend in the TPP process may be determined in part, by the failure strength of the printed material. In other words, the limits of feature size of the printed part may be determined with varying strengths of resist blend. For resist blends with low strength, fine features may not have sufficient strength to survive the development process. Thus increased strength of the resist blend may be preferable for parts with fine features. The mechanical properties of the cured resist, for example, in terms of strength and elasticity of the printed material, may be tuned by selecting the pre-polymer component with a higher number of acrylate functional groups in the pre-polymer.

In various embodiments, the commercially available pre-polymers may include trimethylpropane triacrylate (TMPTA), pentaerythritol triacrylate (PETA), dipentaerythritol penta/hexa-acrylate (DPEP/HA), bisphenol A ethoxylate diacrylate (BPA), etc.

Figure 6:
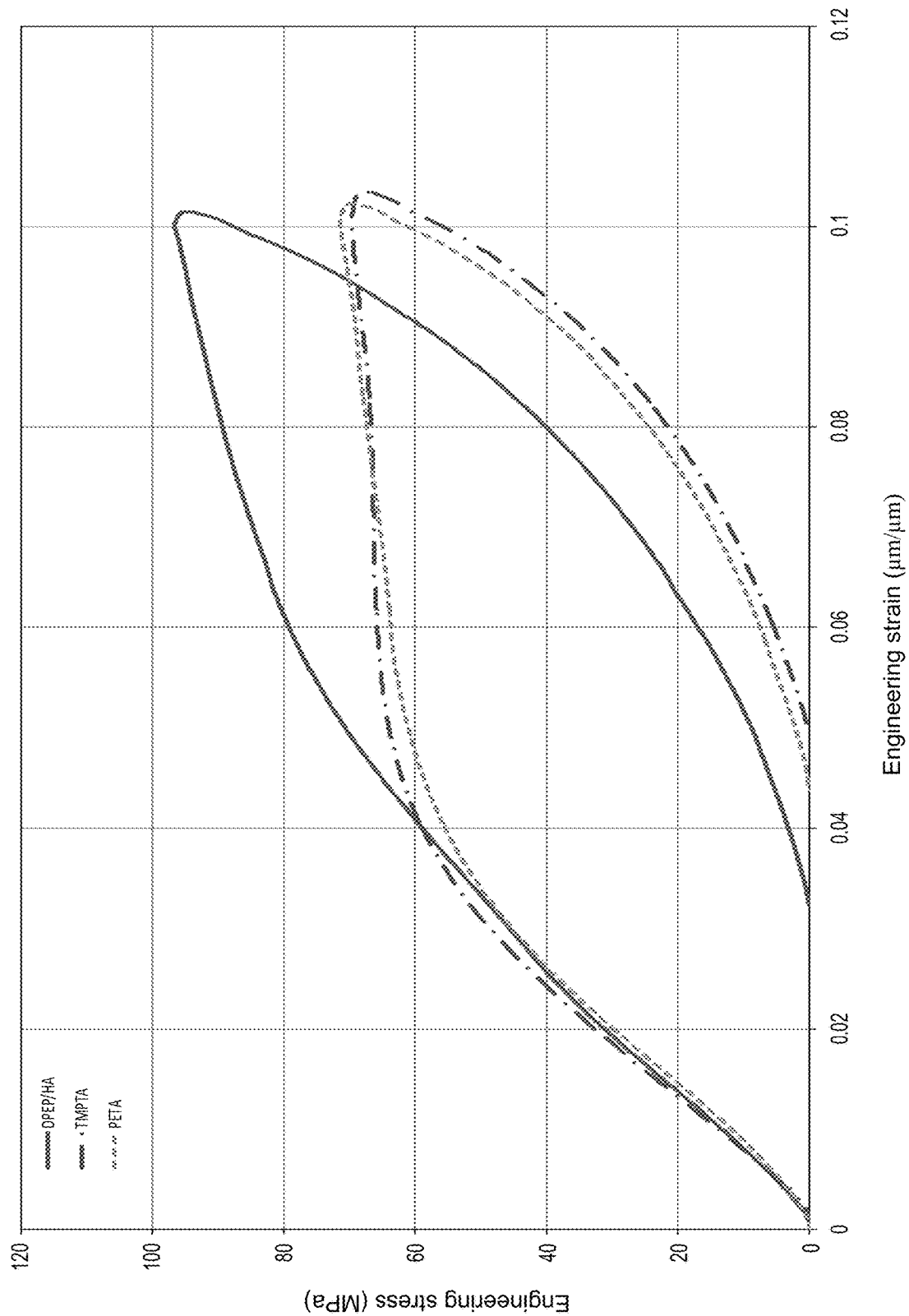
FIG. 6 is a plot diagram of stress and strain of pre-polymers.

FIG. 6 shows the effect of increasing the number of acrylate groups on the pre-polymer component of the resist blend in terms of Engineering stress (Y-axis) and Engineering strain (X-axis). Solid cylindrical parts were printed with resist blends containing different pre-polymers: DPEP/HA (solid line) has 5 to 6 acrylate groups, TMPTA (dash dot line) has 3 acrylate groups (see 602, FIG. 12), and PETA (short dash line) has 3 acrylate groups. The cylindrical shape printed with a resist blend with a pre-polymer having the most acrylate groups, DPEP/HA, shows higher tolerance for stress and strain compared to the cylindrical shapes printed with the resist blends having pre-polymer with fewer acrylate groups.

Tuning the Viscosity of the Uncured Resist

The viscosity of the uncured resist may be tuned. Viscosity of the resist is important for maintaining an intact droplet between the objective lens and the substrate while printing in dip-in mode. The techniques to tune the viscosity of the uncured resist include increasing the molecular weight of the pre-polymers, mixing additives that do not cross link with the pre-polymer, and/or using pre-polymers with groups that lead to hydrogen bonding. These techniques may be used singly or in combination to tune the viscosity of the uncured resist.

Pre-polymers with groups that lead to hydrogen bonding may be used independently to tune the viscosity of the resist without substantially altering the mechanical properties of the uncured resist. For example, TMPTA and PETA have the same number of acrylate functional groups but PETA contains —OH groups and thus is the only pre-polymer out of these two that demonstrates hydrogen bonding. As shown in FIG. 6, the strength and elasticity of the two resists having TMPTA and PETA, respectively, are comparable because both pre-polymers contain the same number of functional acrylate groups.

Design Rules for the Radiopaque Pre-Polymer Compound

As shown above in FIGS. 4 and 5, various embodiments described herein include a method for synthesizing a radiopaque pre-polymer compound that functions in the resist blend to make the polymerized part radiopaque and visible to X-rays. As listed in Table 2, the design rules for a radiopaque pre-polymer compound preferably include low reactivity of the high Z element and high solubility (e.g., at least 90% soluble) of the compound in base pre-polymer. In general, a radiopaque pre-polymer is preferably a pre-polymer that produces a part having nanoscale features that are discernible in X-ray analysis, e.g., nano-CT imaging. Preferred high Z elements include I, Br, Sn, Pb, and Bi.

The high-Z element in the radiopaque pre-polymer compound is covalently bonded to a polymeric backbone of the radiopaque pre-polymer compound. In some approaches, a radiopaque pre-polymer compound may include bromine (Br). In other approaches, the radiopaque pre-polymer compound may include tin (Sn). In yet other approaches, the radiopaque pre-polymer compound may include lead (Pb). In yet another approach, the radiopaque pre-polymer compound may include bismuth (Bi). In an exemplary approach, the radiopaque pre-polymer compound is an iodinated pre-polymer compound 508 as illustrated in FIGS. 5 and 12.

Designing Synthesis of an Iodinated Pre-Polymer with Low Iodine Reactivity

According to one embodiment, synthesis of a radiopaque pre-polymer may include bonding the high-Z element, for example iodine, to an aromatic group (as shown with 2,3,5-triiodobenzoic acid 502, FIG. 5). A densely substituted aromatic group stabilizes the compound whereas alkyl iodines may be too reactive.

Designing Synthesis of an Iodinated Pre-Polymer with High Solubility in Base Pre-Polymer In exemplary embodiments, the high solubility of the iodinated pre-polymer will be assessed by comparing the Hildebrand solubility parameter of the pre-polymer with the base pre-polymer. Iodinated pre-polymers and base pre-polymers that have similar values for the Hildebrand solubility parameter are likely to be soluble in each other. FIG. 7A illustrates examples of the aromatics with covalently bonded high-Z elements that may be considered for synthesis of the radiopaque pre-polymer compound. FIG. 7B illustrates examples of components of the radiopaque pre-polymer that may or may not have a favorable Hildebrand solubility parameter with base pre-polymers in the resist blend. In some approaches of the pre-polymer compound, the densely substituted high Z-element aromatic group may be covalently bound to side chain chemistries that are compatible with UV-curing, for example, acrylates, epoxides, thiolenes, etc.

In a preferred embodiment of a radiopaque pre-polymer compound that provides radiopacity to a printed part, the radiopaque pre-polymer compound may be the iodinated pre-polymer 508 described in FIG. 5. Iodinated pre-polymer compound 508 satisfies the two design rules of Table 2, the densely iodinated aromatic ring provides low iodine reactivity, and the acrylated side chains are soluble in the base pre-polymer TMPTA.

TABLE 3

| Relative Weight % of Iodine | | |
|---|---|---|
| 508 | 602 | Wt % of Iodine |
| 250 mg | 250 mg | 25% |
| 150 mg | 225 mg | 20% |
| 74 mg | 170 mg | 15% |
| 40 mg | 160 mg | 10% |
| 19 mg | 170 mg | 5% |
| — | 500 mg | 0% |

Tuning the Radiopacity of the Resist Blend

The iodinated pre-polymer may be tuned to adjust the radiopacity of the resist blend. Increasing the fraction of the iodinated pre-polymer in the blend may increase the radiopacity of the resist blend and ultimately the printed part. Table 3 shows the relative weight % (wt %) of iodine in resist blends starting with 25 wt % iodine in total weight of resist blend (sum of weights of iodinated pre-polymer compound 508 and base pre-polymer TMPTA 602, see FIG. 12). By serial dilution of the iodinated pre-polymer compound 508, the relative concentrations of wt % iodine in different resist blends decreases proportionately (complemented by increasing amounts of base pre-polymer 602.)

To determine the appropriate degree of opacity of a printed part for X-ray absorption, the linear attenuation coefficient (LAC) calculation may provide optimal concentration of iodinated pre-polymer in the resist blend. The calculation of LAC of the resist may be obtained from the elemental mass attenuation coefficient (MACi), mass fraction of the elements ($\chi_i$), and the bulk material density ($\rho$) as shown in Equation 2 below.

$$LAC = \rho \Sigma_i^n MAC_i \chi_i \quad \text{Equation 2}$$

Figure 8:
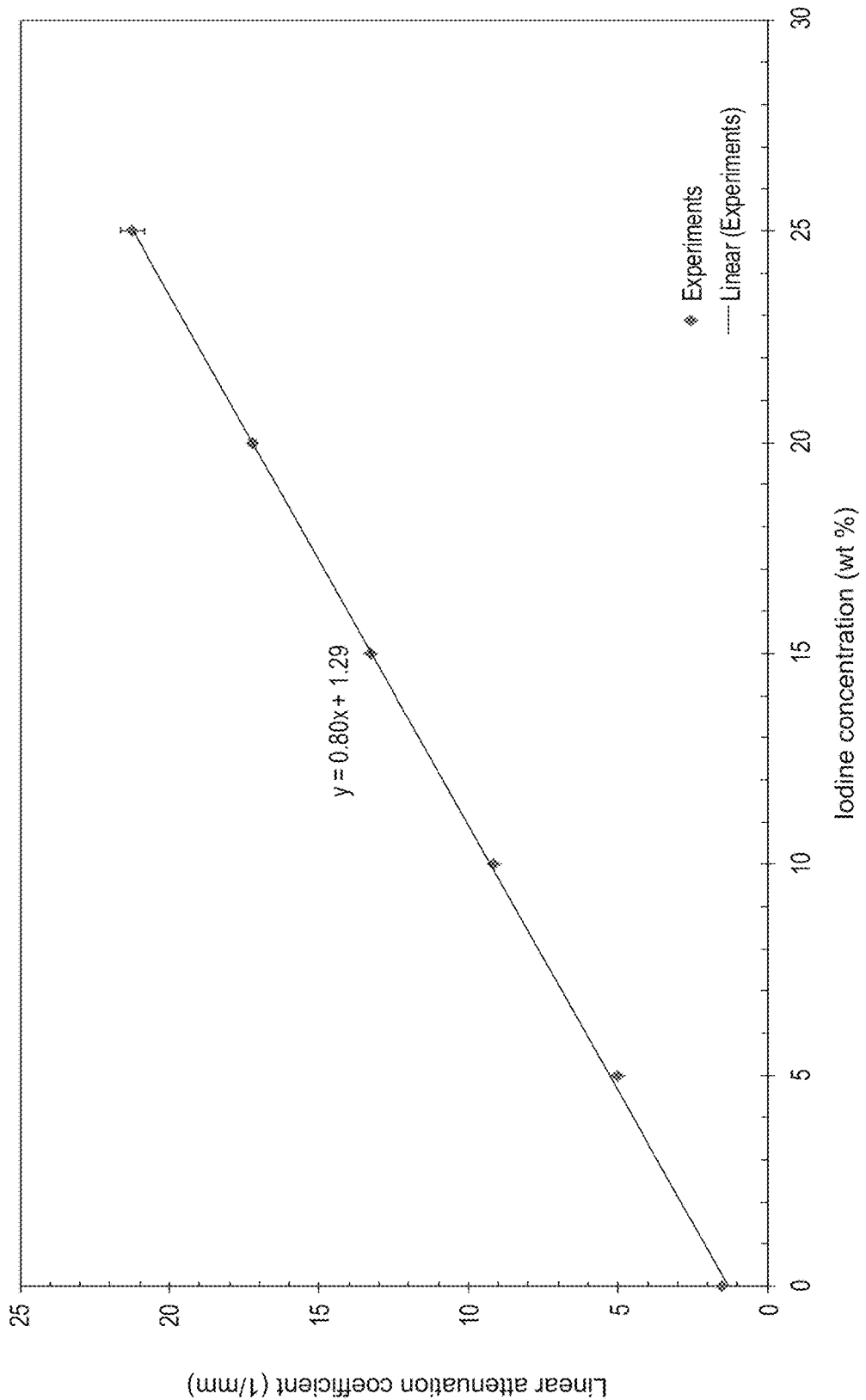
FIG. 8 is a plot diagram of Linear Attenuation Coefficients of iodinated pre-polymer compound at serial dilutions of iodine.

Table 4 lists the elemental mass attenuation coefficient ($MAC_i$) for common elements including low-Z elements hydrogen, carbon, nitrogen and oxygen compared to high-Z elements bromine and iodine. The linear attenuation coefficients (LAC) measured during X-ray imaging of parts printed with resist blends of different iodine concentrations (5 wt %, 10 wt %, 15 wt %, 20 wt %, 25 wt %) are plotted on the graph in FIG. 8. The results show the linear relationship between increasing iodine concentration in the resist blends with increasing linear attenuation coefficient. This relationship shows that the iodinated pre-polymer compound as a component of the resist blend may increase the X-ray LAC of the TPP resist from approximately 1.52 $mm^{-1}$ (radiolucent) to over 21.25 $mm^{-1}$ (radiopaque). Thus, the radiopacity of the printed part may be tuned using the mixing rule presented in Equation 3 (see next section).

TABLE 4

| Element | MAC |
| --- | --- |
| Hydrogen, H | 0.4 |
| Carbon, C | 4.6 |
| Nitrogen, N | 7.6 |
| Oxygen, O | 11.6 |
| Bromine, Br | 90.3 |
| Iodine, I | 292.2 |

Design Rules for Additive Pre-Polymer

Matching the Refractive Index of the Resist Blend to the Objective Lens of the Printer.

Looking to Tables 1 and 2, the function of the additive pre-polymer is to tune the resist blend to obtain a desired refractive index. In an exemplary embodiment, the Refractive Index of the resist blend may be about 1.52 to match the Refractive Index of an objective lens used for TPP.

The refractive index of the resist blend used for printing of three dimensional tall structures may reflect the quality of the resulting structure. In various embodiments, the refractive index of the resist blend may be about equal to the refractive index of an objective lens of a TPP lithography process that uses the resist blend.

When the refractive index of the resist is substantially different (for example, different by greater than at least 0.015) from the refractive index of the objective lens, the light intensity at the focal spot may be lower than the desired value. Spherical aberrations at the focal spot may be responsible for lower than desired value of light intensity. The intensity of the focal spot diminishes with increasing length of the optical path. Thus, writing tall structures may be difficult as the intensity drops below the threshold writing intensity and below a critical resist layer thickness. Furthermore, the presence of multiple focal planes at different depths generated by spherical aberrations may axially smear the features.

Figure 9B:
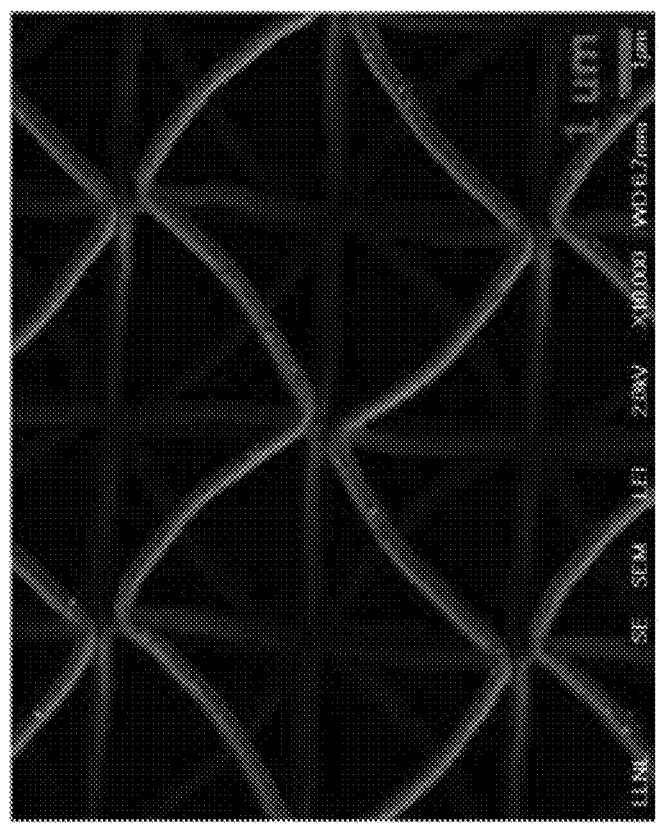
FIG. 9B is a scanning electron micrograph images of a 3D printed part according to one embodiment.
Figure 9A:
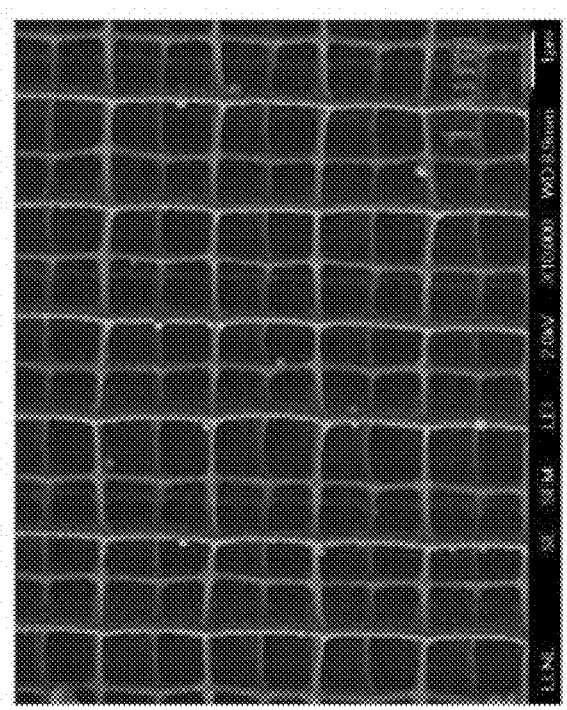
FIG. 9A is a scanning electron micrograph images of a 3D printed part according to one embodiment.

The effects of refractive index on quality of writing are shown in the scanning electron micrograph (SEM) images of 3D printed parts in FIGS. 9A and 9B. In a case in which the resist blend has a lower refractive index than the objective lens (1.50 for resist versus 1.52 for lens), then the printed structures may have axially smeared features as seen in FIG. 9A. The cross bars exhibit web-like geometry which is caused by the oval being elongated (rather than printing a sharp oval bar) along the laser beam axis (the direction perpendicular to both bars and into the plane of the figure). Sharper features are shown in FIG. 9B in which the refractive index of the resist blend matched the refractive index of the objective lens of the printer.

The refractive index of the resist blend may be tuned by adding components that raise or decrease the refractive index of the resist blend. The mixing rule may be approximated as:

$$n = \Sigma_i^k n_i f_i \quad \text{Equation 3}$$

In Equation 3, n is the refractive index of the mixture, $n_i$ is the refractive index of the $i^{th}$ component, $f_i$ is the volume fraction of the $i^{th}$ component, and the resist consists of k distinct components. The refractive index of commonly used acrylate pre-polymers, and possibly used as base pre-polymers 9 in various embodiments described herein, are summarized in Table 5.

TABLE 5

| | Pre-polymer | Refractive Index |
| --- | --- | --- |
| TMPTA | Trimethylolpropane triacrylate | 1.474 |
| PETA | Pentaerythritol triacrylate | 1.483 |
| DPEP/HA | Dipentaerythritol penta/hexa-acrylate | 1.490 |
| BPA | Bisphenol A ethoxylate diacrylate | 1.545 |

Figure 10:
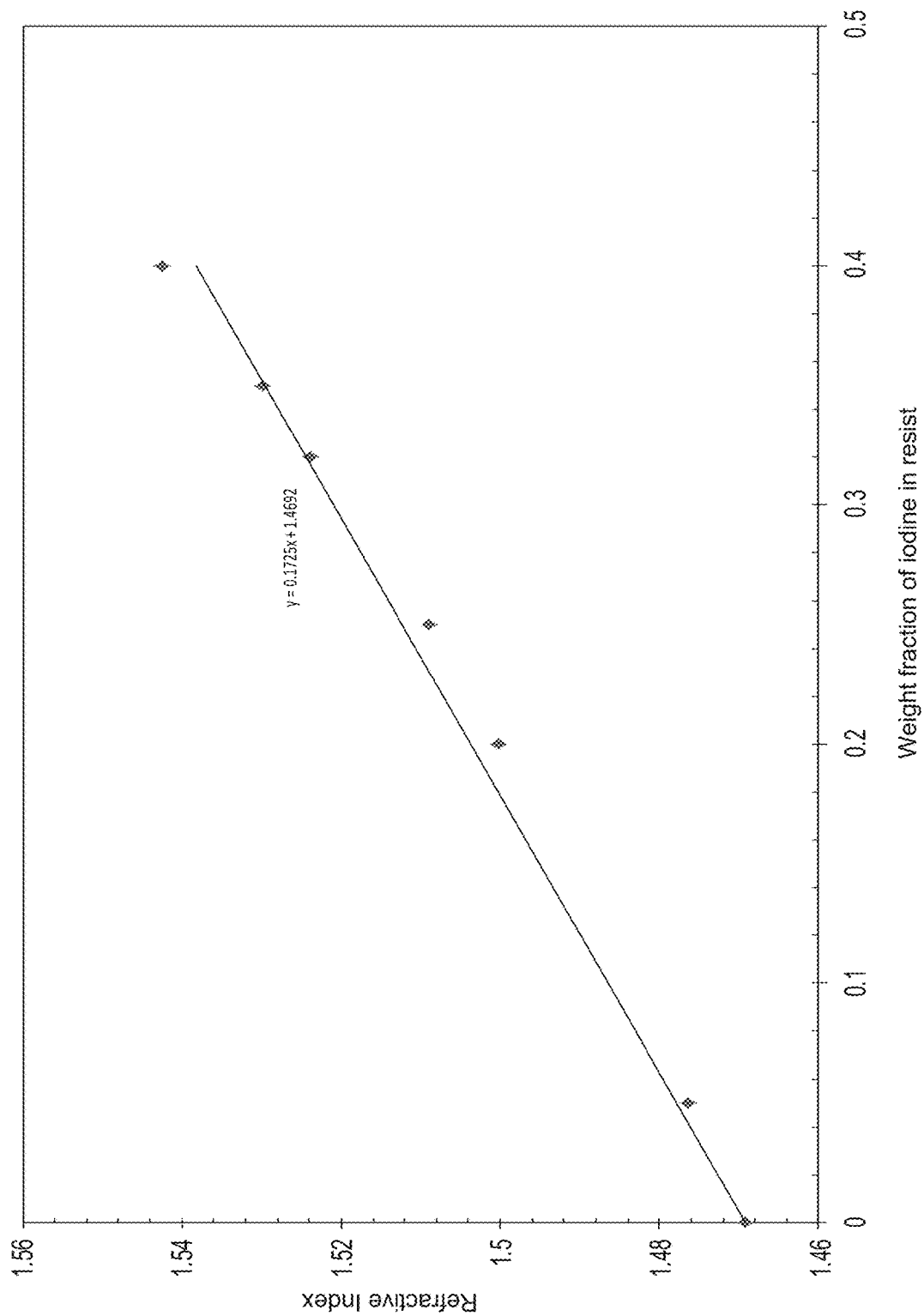
FIG. 10 is a plot diagram of the estimation of the refractive index of the iodinated pre-polymer according to one embodiment.

FIG. 10 shows an estimation of the refractive index for the iodinated pre-polymer compound 508. The refractive index was estimated empirically by varying the concentration of the iodinated pre-polymer with the base pre-polymer 602 TMPTA (FIG. 12) and DMF solvent (with a refractive index of 1.43) in a three-component mixture. Using Equation 3 to plot the graph of FIG. 10, the refractive index of the iodinated pre-polymer compound 508 may be estimated to be 1.564 by extrapolating the experimental data to an iodine weight fraction of 0.548.

In some approaches, the refractive index of the iodinated pre-polymer+base polymer may be independently tuned by adding a third pre-polymer with high refractive index (for example, BPA).

Ratios of Components of Radiopaque Resist Blend

Table 6 provides the design rules for determining the ratios of each component in a radiopaque resist blend according to some embodiments.

TABLE 6

| | | Design Rules for Ratio of Resist Blend |
| --- | --- | --- |
| # | Component | Design Rule for Ratio |
| 1 | Photoinitiator | Concentration may be sufficiently high to obtain writing but not so high that indiscriminate bulk polymerization is initiated. Experimentally found to be 0.01 to 1.0 wt %. |
| 2 | Base Pre-polymer | See #4 |
| 3 | Iodinated Pre-polymer | Ratio based on desired radiopacity that is determined by Equation 2. For high contrast X-ray imaging, desired linear attenuation coefficient is 9 $mm^{-1}$ to 21 $mm^{-1}$ corresponding to 18 to 45 wt % of iodinated pre-polymer. |
| 4 | Additive Pre-polymer for RI tuning | Ratio of base pre-polymer and additive pre-polymers is selected such that the net RI of the blend is 1.52 using the mixing rule presented in Equation 3. |
| 5 | Inhibitor | There should be enough inhibitor to prevent spontaneous polymerization prior to exposure to light, but not so much as to prevent polymerization upon exposure to light. Typically in the range of 0.02 to 0.08 wt %. |
| 6 | Solvent | As required but less than 10%. For example, TMPTA + iodinate pre-polymers need solvents; (PETA or DPEP/HA) + iodinated pre-polymer do not need solvents. |

TABLE 7

Ratios for Resist Blend

| # | Component | Weight (%) | Function | Examples | Synthesis |
|---|---|---|---|---|---|
| 1 | Photoinitiator | Range: 0.01 to 1.0 Typical: 0.1 to 0.5 | To absorb light and generate reactive species | 604, FIG. 12 | Conventional methods |
| 2 | Base Pre-polymer | Range: 30 to 100 Typical: 40 to 85 | Forms the backbone of cured material | TMPTA, PETA DPEP/HA | Commercially available |
| 3 | Iodinated Pre-polymer | Range: 0 to 70 Typical: 18-45 | To make the polymerized material radiopaque | "I3" pre-polymer 508, FIG. 5 & 12 | Newly synthesized molecule |
| 4 | Additive Pre-polymer | Range: 0 to 45 Typical: depends on amount needed to increase RI to 1.52 | To tune the refractive index | BPA | Commercially available |
| 5 | Inhibitor | Typical: 0.02-0.08 | To control polymerization, to limit voxel size, to extend pot-life by preventing pre-polymerization | MEHQ | Commercially available |
| 6 | Solvent | Range: <10 Typical: <1 | To increase solubility of iodinated pre-polymer in resist blend | DMF | Commercially available |

Table 7 summarizes the ratios for optimal composition of the radiopaque resist blend according to some embodiments.

In one embodiment, the photoinitiator may be purchased, or synthesized using conventional methods. In an exemplary embodiment, the photoinitiator may have a high two photon cross section (see FIG. 12, photoinitiator 604) and preferably generate radicals instead of generating fluorescence.

In some embodiments, the concentration of photoinitiator may be sufficiently high to initiate writing. In some approaches, the concentration of photoinitiator may be determined by the concentration of inhibitor in the resist blend. In an exemplary embodiment, the photoinitiator may be present in an amount in a range of about 0.01 to about 0.10 wt % of resist blend, preferably in the range of about 0.1 to 0.5 wt % of resist blend.

The effectiveness of a given photoinitiator and photoinitiator concentration may be closely related to the concentration of an inhibitor present in the resist. In some embodiments, the inhibitor concentrations may be typically between about 0.02 to about 0.08 wt %. An inhibitor may prevent bulk polymerization of the resist. In addition, an inhibitor may increase the pot-life of the resist by preventing spontaneous polymerization. During printing, an inhibitor may help control the growth of the voxel by limiting the extent of polymerization.

For example, in a case of radical-mediated acrylate polymerization, the first wave of radicals produced by the photoinitiator upon exposure to a suitable light source may be consumed by the local inhibitor concentration. The second wave of radicals may initiate local polymerization leading to cured material. The extent to which polymerization can proceed may be limited by the remaining inhibitor that was not initially consumed by the first wave of radicals.

In some embodiments, the base pre-polymer and the additive pre-polymer may be selected such that the net Refractive Index of the resist blend is 1.52 using the mixing rule of Equation 3. In one embodiment the base pre-polymer may be present in an amount in a range of about 30 to about 100 wt % of resist blend, preferably in a range of about 40 to about 85 wt % of resist blend (for example, see FIG. 12, TMPTA 602).

In some embodiments of the resist blend, an additive pre-polymer may be present in an amount in a range of greater than 0 to about 45 wt % of resist blend. The amount of additive pre-polymer may be tuned to result in the refractive index of 1.52 of the resist blend.

In some embodiments, the ratio of iodinated pre-polymer in the resist blend may be based on desired radiopacity that may be determined by Equation 2. According to one embodiment, the resist blend described herein may be radiopaque. In some embodiments for high contrast X-ray imaging, the resist blend may have a linear attenuation coefficient (LAC) in the range of about 9 mm$^{-1}$ to 21 mm$^{-1}$ that may correspond to about 18 wt % to 45 wt % of iodinated pre-polymer.

In an exemplary embodiment of the resist blend, the iodinated pre-polymer compound (for example, see FIGS. 5 and 12, iodinated pre-polymer compound 508) may be present in an amount in a range of greater than 0 to about 70 wt % based on a total weight of the resist blend.

In various embodiments, solvents that increase the solubility of the pre-polymers may be used, for example DMF, THF, etc and may be commercially available. Ideally, the boiling point/vapor pressure of the solvent additive is high. Low boiling point solvents tend to evaporate during the printing process leading to precipitation of the resist components.

In some approaches, TMPTA+iodinated pre-polymers may need to be present in solvent. In other approaches, PETA or DPEP/HA+iodinated pre-polymer may not need to be present in solvent. In some embodiments of the resist blend, the solvent may be present in an amount in a range of about 0 to less than 10 wt % of resist blend.

Method to Form the Radiopaque Resist Blend

Figure 11:
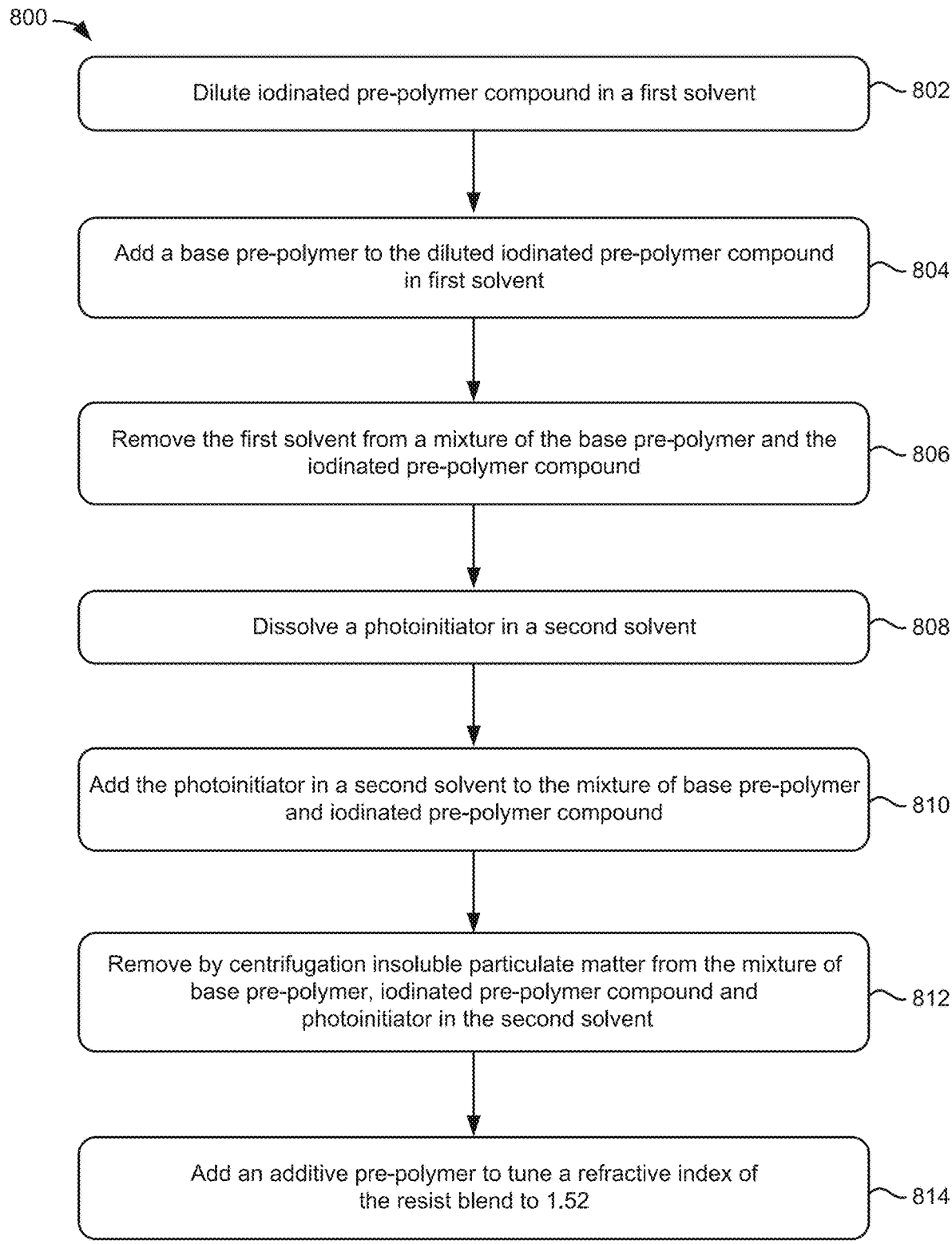
FIG. 11 is a flow diagram of the formation of an optically clear, radiopaque resist blend according to one embodiment.

FIG. 11 shows a method 800 for forming an optically clear, radiopaque resist blend, in accordance with one embodiment. As an option, the present method 800 may be implemented to create resist blends such as those shown in the other FIGS. described herein. Of course, however, this method 800 and others presented herein may be used to form photonic- and mechanical metamaterials, low density foams, micro-fluidic devices, biomimetic scaffolding and micro-machines, which may or may not be related to the illustrative embodiments listed herein. Further, the methods presented herein may be carried out in any desired environment. Moreover, more or less operations than those shown in FIG. 11 may be included in method 800, according to various embodiments. It should also be noted that any of the aforementioned features may be used in any of the embodiments described in accordance with the various methods.

According to one embodiment, the method 800 for forming an optically clear resist blend for two photon polymerization, begins with step 802 of diluting an iodinated pre-polymer compound in a first solvent, for example THF.

Step 804 of method 800 includes adding a base pre-polymer to the diluted iodinated pre-polymer compound in first solvent. In exemplary embodiments, the base pre-polymer, for example, TMPTA (602 in FIG. 12) may be added to the iodinated pre-polymer compound (508 in FIG. 5) in THF.

Looking to FIG. 11, in one embodiment of method 800, step 806 involves removing the first solvent from a mixture of the base pre-polymer and the iodinated pre-polymer compound. In some approaches, the techniques known in the art for removing the first solvent may include vortexing the mixture followed by treatment with compressed air to remove first solvent, for example, THF, for a period of 12 hours.

In one embodiment of method 800, step 808 includes dissolving a photoinitiator in a second solvent. For example, a photoinitiator (604 in FIG. 12) may be dissolved in DMF (606 in FIG. 12).

In one embodiment of method 800, step 810 includes adding the photoinitiator in a second solvent to the mixture of base pre-polymer and iodinated pre-polymer compound. For example, looking to FIG. 12, the photoinitiator 604 in DMF 606 may be added to a mixture of iodinated pre-polymer compound 508/base pre-polymer 602 (to a final concentration of photoinitiator of 0.2 wt % of blend).

Referring back to FIG. 11, one embodiment of method 800, step 812 includes removing by centrifugation insoluble particulate matter from the mixture of base pre-polymer, iodinated pre-polymer compound, and photoinitiator in the second solvent.

In one embodiment of method 800, step 814 includes adding an additive pre-polymer to tune a refractive index of the resist blend to 1.52.

In preferred embodiments of method 800, the resist blend may be thermally unstable. For example, epoxide containing pre-polymers are prone to polymerization at elevated temperatures so that method 800 carried out at lower temperatures is the preferred embodiment for such formulations.

In other embodiments of the method to form the radiopaque resist blend, the resist components may be combined together in a single container while applying heat (<100° C.) to generate a homogeneous mixture. This method is a preferred embodiment for thermally stable pre-polymers, for example, acrylic pre-polymers.

In one exemplary embodiment, a method for patterning the optically clear, radiopaque resist blend formed from methods described herein include performing two photon polymerization on the resist blend to create a three dimensional structure with nanometer-size features.

FIG. 12 depicts examples of the components of an illustrative resist blend 600 for an optically clear resist blend, in accordance with one embodiment. As an option, the present blend 600 may be implemented in conjunction with features from any other embodiment listed herein, such as those described with reference to the other FIGS. Of course, however, such a blend 600 and others presented herein may be used in various applications and/or in permutations which may or may not be specifically described in the illustrative embodiments listed herein. Further, the blend 600 presented herein may be used in any desired environment.

Exemplary components of the illustrative radiopaque resist blend 600 formed from method 800 in FIG. 11 is depicted in FIG. 12 according to one embodiment. The optically clear resist blend 600 includes an iodinated pre-polymer compound 508, a photoinitiator 604, a base pre-polymer 602, and a solvent 606.

Examples of TPP Lithography using Optically Clear, Radiopaque Resist Blend

The following experimental results pertain to illustrative embodiments of the novel optically clear, radiopaque resist blend. It is important to note that the following illustrative embodiments do not limit the invention in anyway. It should also be understood that variations and modifications of these illustrative embodiments may be made by those skilled in the art without departing from the spirit and scope of the in A 25 wt % iodinated radiopaque resist blend with a refractive index of 1.509, described herein, was used as the photoresist in conventional (FIGS. 13C and 13D) mode and dip-in mode (FIGS. 13E and 13F) TPP lithography. FIGS. 13A and 13B show the Computer Aided Design (CAD) rendering of the expected log-pile structures to be printed using TPP lithography in each mode with the 25 wt % iodine resist blend. The TPP lithography using both modes generated 30 µm wide log-pile structures with 1 µm spacing between each line and 0.6 µm between each layer.

Although the polymerization process was identical in the two modes, the practical fabrication performance metrics of the two modes were different. The conventional mode limited structures to a height of 30 µm whereas the dip-in mode allowed fabrication of structures with heights greater than 1 mm.

Both modes were carried out with a 63× NA 1.4 objective lens. The structures printed in the dip-in mode with the 63× NA 1.4 objective lens appear less well-defined and need higher laser powers (40 mW versus 10 mW at a scan speed of 10 mm/sec) (see FIGS. 13E and 13F) compared to corresponding structures printed in conventional mode (FIGS. 13C and 13D). The inventors believe that this was due to increasing aspect ratio of the features of the printed parts (see FIG. 2A) because there was a mismatch in the refractive index of the 25 wt % iodine resist blend and the 63× NA 1.4 objective lens. The mismatched refractive indices of the resist and the objective lens did not appear to adversely affect the resolution of the printed part using the conventional mode (FIGS. 13C and 13D)

Using an objective with an adjustable focus, a 25× NA 0.8 objective lens that is less sensitive to refractive index, with the dip-in mode (FIGS. 13G and 13H) restored clarity of the printed parts (FIG. 13H) compared to corresponding structures printed in conventional mode (FIG. 13D).

FIGS. 14A-14D show that with the optically clear, radiopaque resist blend described herein, parts with small feature sizes may be printed. The SEM images show increasing magnifications from 25 µm (FIG. 14A) to 100 nm (FIG. 14D) of the hexagonal lattice printed with the 25 wt % iodine resist blend in dip-in mode with a 63× NA 1.4 objective lens. FIG. 14E shows the CAD rendering of a hexagonal structure of which each hexagon is approximately 4 µm wide. FIG. 14C with a relative magnification of 1 µm shows the printed part has features oriented as expected from the CAD rendering (FIG. 14E). Taken together, these results show the radiopaque formulation of resist blend with iodinated pre-polymer as described herein generated structures with submicron resolution under various printing conditions.

X-Ray CT Images of Printed Parts Generated with Optically Clear, Radiopaque Resist Blend.

Figures 15A, 15B:
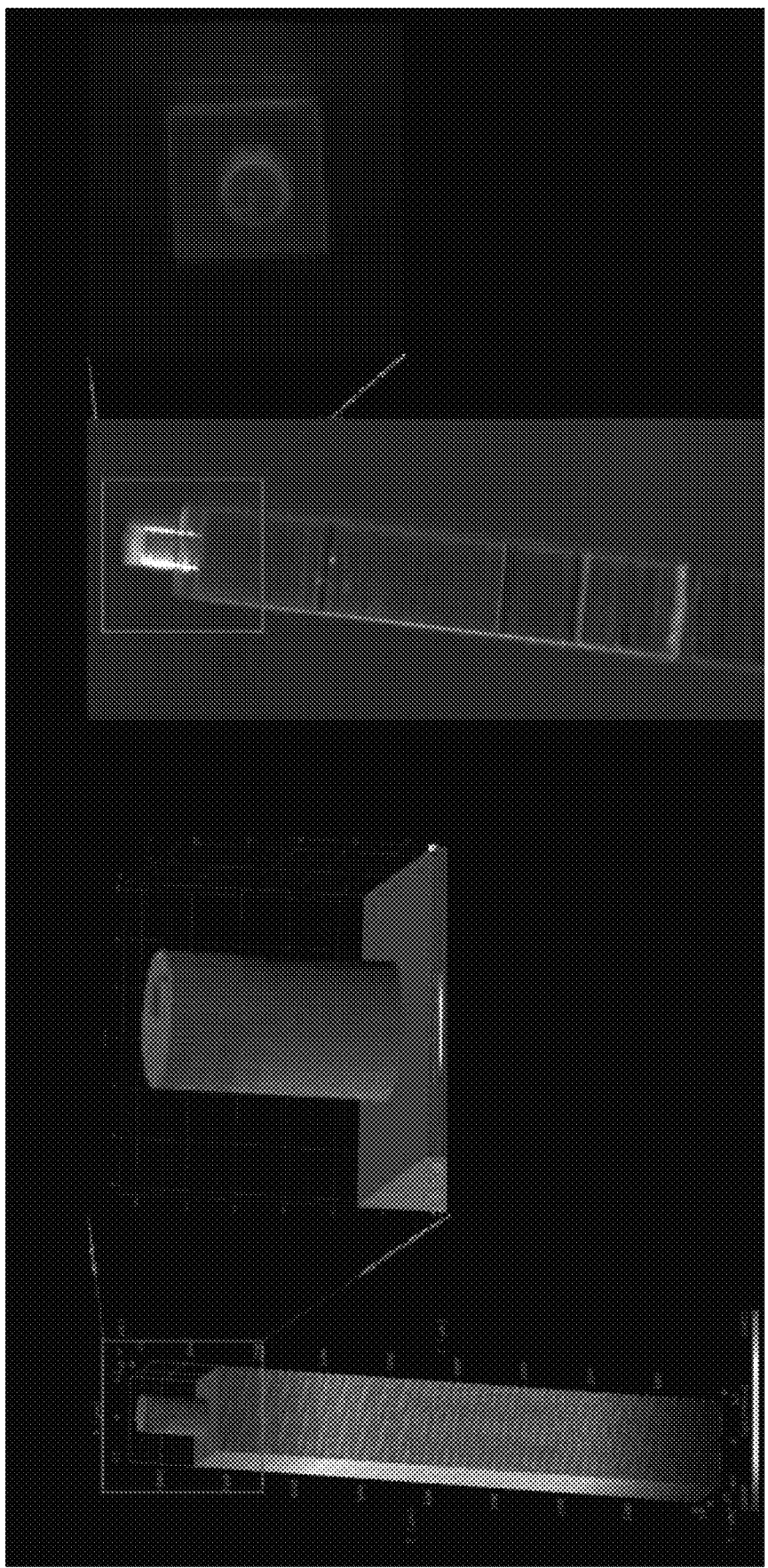
FIG. 15A is a CAD drawing of CT test object according to one embodiment.
FIG. 15B is an optical microscope image of CT test object according to one embodiment.

A CT test object was generated to test X-ray attenuation of a printed part by TPP lithography using the optically clear radiopaque resist blend described herein. FIG. 15A shows the CAD rendering of the CT test object. The top section of the CT test object is a right circular cylinder diameter of 55 μm and height of 97.5 μm. The base pillar of the CT test object measured at 750 μm tall with a 137.5 μm by 125.0 μm base. FIG. 15B shows the surface imaging of the CT test object by an optical microscope. The view looking down on the top of the CT test object is shown in the outset image of FIG. 15B.

Figures 16A, 16B:
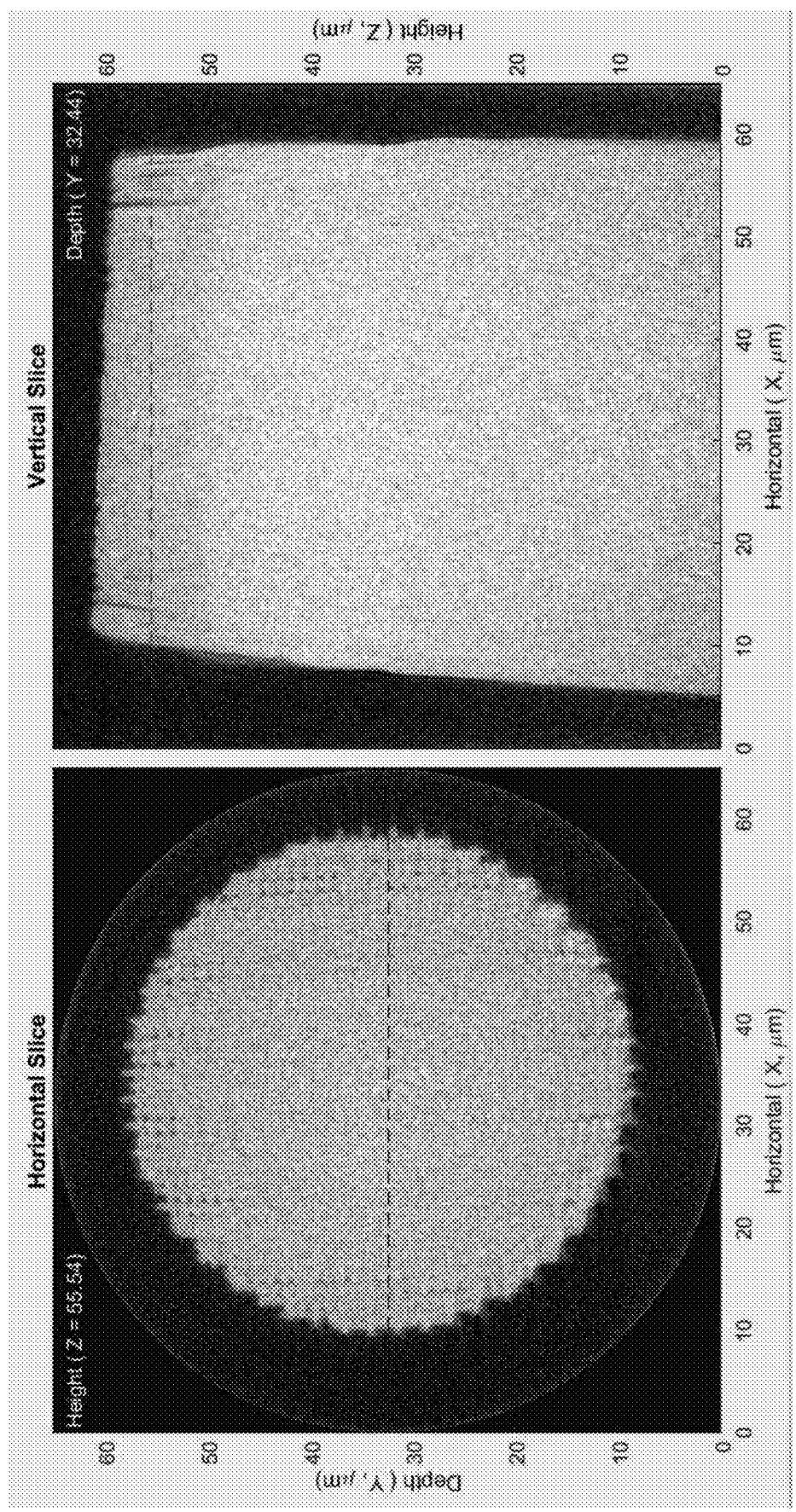
FIG. 16A is an image of a horizontal slice of a 3D-CT reconstruction of the CT test object according to one embodiment.
FIG. 16B is an image of a vertical slice of a 3D-CT reconstruction of the CT test object according to one embodiment.

X-ray attenuation of the CT test object was verified with nano-CT performed on the commercially available Zeiss Xradia UltraXRM-L200 system with an 8 keV X-ray source. Two slices from the reconstructed 3D image depicting the internal features of the part are shown in FIGS. 16A and 16B. A horizontal slice of the top section of test object is shown in FIG. 16A. The height of the horizontal slice, 55.54 μm, is about the same as the diameter measured in the top section of the CAD rendering of the CT test object in FIG. 15A. A vertical slide of the CT test object is shown in FIG. 16B. The AM parts fabricated with radiopaque resist showed an increase in X-ray linear attenuation coefficient by a factor of 10 to 20 times, thereby showing that the AM parts were radiopaque. These X-ray CT images of the radiopaque AM part show the internal structure of the CT test object and confirm the original CAD rendering of features that are not visible through surface imaging techniques.

In use, the optically clear, radiopaque resist blend may be used for TPP additive manufacturing to generate submicron building blocks.

The methods for forming the resist blend and the resist blend itself are useful for fabrication of high-contrast polymer parts for calibration of X-ray CT systems. The resist blend described herein may replace existing photopolymers and may generate AM parts that are suitable for inspection via X-ray CT. The generation of parts that may be inspected by X-ray CT is essential in transitioning polymer AM technologies from the state of research curiosities to well-characterized systems capable of fabricating functional parts to tighten design tolerances.

The radiopaque polymer AM parts generated using methods and compounds described herein may be used in photonic crystals (sensors), mechanical metamaterials (low-density, high-strength engineered metamaterials), and microfluidics (for biomedical diagnostic chips).

The inventive concepts disclosed herein have been presented by way of example to illustrate the myriad features thereof in a plurality of illustrative scenarios, embodiments, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A resist blend of comprising:
   a radiopaque pre-polymer compound, wherein the radiopaque pre-polymer compound is an iodinated pre-polymer having a structural formula as follows:

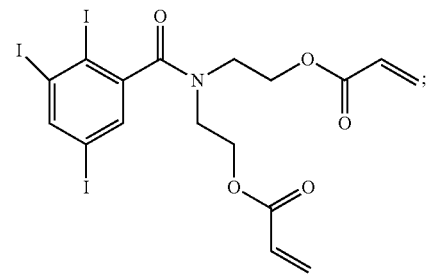 [SMILES: C=CC(=O)OCCN(CCOC(=O)C=C)C(=O)c1cc(I)cc(I)c1I]

a photoinitiator;
   a polymerization inhibitor; and
   a base pre-polymer,
   wherein the resist blend has a refractive index of 1.52±0.015.

2. The iodinated pre-polymer as recited in claim 1, wherein the iodinated pre-polymer contains iodine in a range of about 53 wt % to about 56 wt % based on a total weight of the iodinated pre-polymer.

3. The iodinated pre-polymer as recited in claim 1, wherein the iodinated pre-polymer is in solid form.

4. The iodinated pre-polymer as recited in claim 1, wherein the iodinated pre-polymer is soluble in the base pre-polymer.

5. The resist blend of claim 1, wherein the base pre-polymer is present in a range of at least 40 to 85 wt % of resist blend.

6. The resist blend of claim 1, wherein the photoinitiator is present in an amount in a range of about 0.01 to about 0.10 wt % of resist blend.

7. The resist blend of claim 1, wherein the radiopaque pre-polymer compound is present in an amount in a range of greater than 0 to about 70 wt % of resist blend.

8. The resist blend of claim 1, wherein the inhibitor is present in an amount in a range of about 0.02 to about 0.08 wt % of resist blend.

9. The resist blend of claim 1, wherein the base pre-polymer is present in an amount in a range of about 30 to about 100 wt % of resist blend.

10. The resist blend of claim 1, further comprising an additive pre-polymer present in an amount in a range of greater than 0 to about 45 wt % of resist blend wherein the amount of additive pre-polymer is tuned to result in the resist blend having the refractive index of 1.52±0.015.

11. The resist blend of claim 1, wherein a solvent is present in an amount in a range of greater than 0 to less than 10 wt % of resist blend.

12. The resist blend of claim 1, wherein the resist blend is radiopaque.

13. The resist blend of claim 1, wherein the resist blend has a linear attenuation coefficient in a range of about 9 $mm^{-1}$ to 21 $mm^{-1}$.

14. A composition of an optically clear resist blend for additive manufacturing, the composition comprising:
   a radiopaque iodinated pre-polymer compound, wherein the iodinated pre-polymer compound has a structural formula as follows:

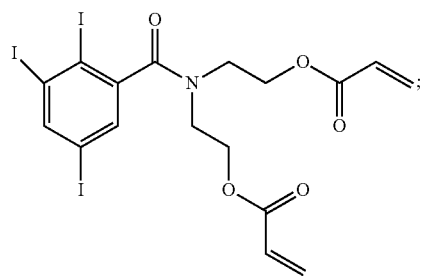 [SMILES: C=CC(=O)OCCN(CCOC(=O)C=C)C(=O)c1cc(I)cc(I)c1I]

a photoinitiator;
a polymerization inhibitor; and
a base pre-polymer.

16. The composition of claim 14, wherein a concentration of iodine in the iodinated pre-polymer compound is in a range of about 53 wt % to about 56 wt % based on a total weight of the iodinated pre-polymer compound.

16. The composition of claim 14, wherein the iodinated pre-polymer compound is in solid form.

17. The composition of claim 14, wherein the iodinated pre-polymer compound is soluble in the base pre-polymer.

* * * * *